United States Patent
Liepold et al.

(10) Patent No.: US 11,020,032 B2
(45) Date of Patent: Jun. 1, 2021

(54) FLUID SAMPLING APPARATUS AND METHOD

(71) Applicants: Lars Otto Liepold, St. Louis Park, MN (US); Darren Patrick Liepold, St. Louis Park, MN (US)

(72) Inventors: Lars Otto Liepold, St. Louis Park, MN (US); Darren Patrick Liepold, St. Louis Park, MN (US)

(*) Notice: Subject to any disclaimer, the term of this patent is extended or adjusted under 35 U.S.C. 154(b) by 17 days.

(21) Appl. No.: 15/950,664

(22) Filed: Apr. 11, 2018

(65) Prior Publication Data

US 2019/0015031 A1 Jan. 17, 2019

Related U.S. Application Data

(63) Continuation of application No. 14/216,761, filed on Mar. 17, 2014, now abandoned.
(Continued)

(51) Int. Cl.
*A61B 5/15* (2006.01)
*G01N 33/49* (2006.01)
*B01L 3/00* (2006.01)

(52) U.S. Cl.
CPC .. *A61B 5/150358* (2013.01); *A61B 5/150022* (2013.01); *A61B 5/150305* (2013.01); *A61B 5/150343* (2013.01); *A61B 5/150755* (2013.01); *A61B 5/150763* (2013.01); *A61B 5/150786* (2013.01); *B01L 3/5029* (2013.01);
(Continued)

(58) Field of Classification Search
None
See application file for complete search history.

(56) References Cited

U.S. PATENT DOCUMENTS

2007/0255175 A1* 11/2007 Sangha .............. A61B 10/0045
600/572
2009/0024060 A1 1/2009 Darrigrand
(Continued)

FOREIGN PATENT DOCUMENTS

EP 2420831 2/2012
EP 2484448 8/2012
(Continued)

OTHER PUBLICATIONS

General Electric Company, GE Healthcare, "Sample Collection Cards & Kits," (2014); http://www.whatman.com/903ProteinSaverCards.aspx.
(Continued)

*Primary Examiner* — Kathryn Wright
(74) *Attorney, Agent, or Firm* — Billion & Armitage

(57) ABSTRACT

The present invention relates generally to a sampling apparatus and a method for bodily fluids, and, more specifically, a blood sampling apparatus and a method for using the same. A blood collection system includes a housing having at least one open end, and an absorbent material positioned within the housing. The absorbent material has at least one end positioned proximate the at least one open end of the housing. A method of collecting blood samples includes positioning an absorbent material near a source of blood, holding the absorbent material with a housing, the absorbent material absorbing a volume of blood, and moving the housing and absorbent material to a position where the absorbent material can dry.

11 Claims, 19 Drawing Sheets

Related U.S. Application Data

(60) Provisional application No. 61/798,535, filed on Mar. 15, 2013, provisional application No. 62/634,344, filed on Feb. 23, 2018.

(52) U.S. Cl.
CPC ............ *B01L 3/5082* (2013.01); *G01N 33/49* (2013.01); *B01L 2200/141* (2013.01); *B01L 2300/0832* (2013.01)

(56) References Cited

U.S. PATENT DOCUMENTS

| | | | |
|---|---|---|---|
| 2011/0204084 A1 | 8/2011 | Aronowitz | |
| 2013/0011042 A1* | 1/2013 | Satish | G06K 9/00 |
| | | | 382/134 |
| 2013/0023007 A1* | 1/2013 | Zahniser | G06K 9/0014 |
| | | | 435/34 |
| 2013/0116597 A1* | 5/2013 | Rudge | A61B 5/150305 |
| | | | 600/575 |

FOREIGN PATENT DOCUMENTS

| | | |
|---|---|---|
| EP | 1718410 | 1/2013 |
| WO | 2014058615 A3 | 7/2014 |

OTHER PUBLICATIONS

Spot On Sciences, "HemaSpot™," (2014); http://www.spotonsciences.com/.

* cited by examiner

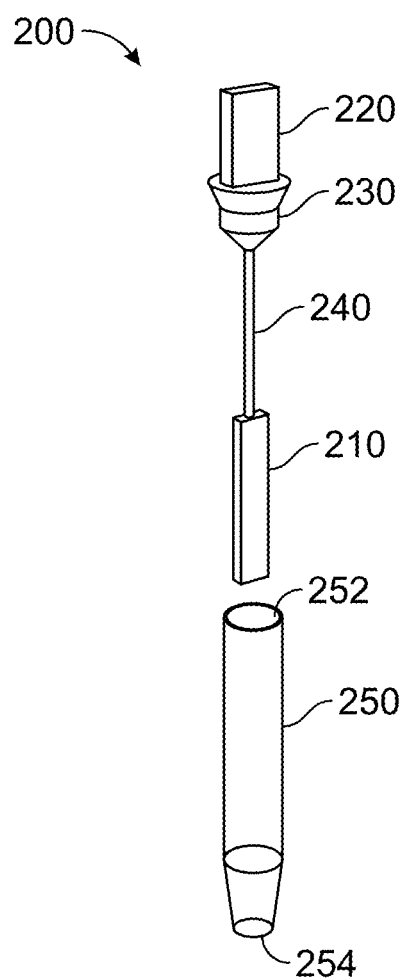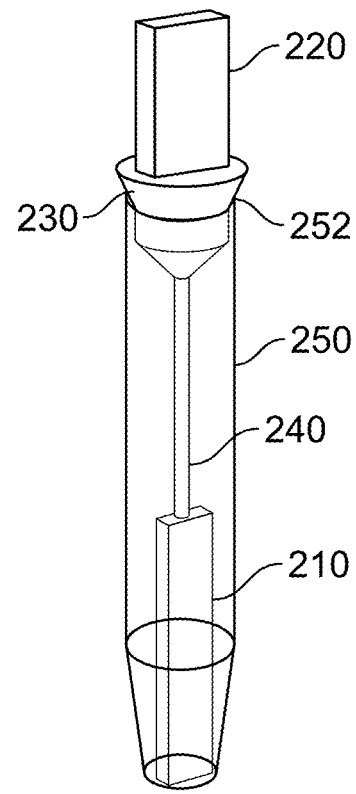
FIG. 2  FIG. 3

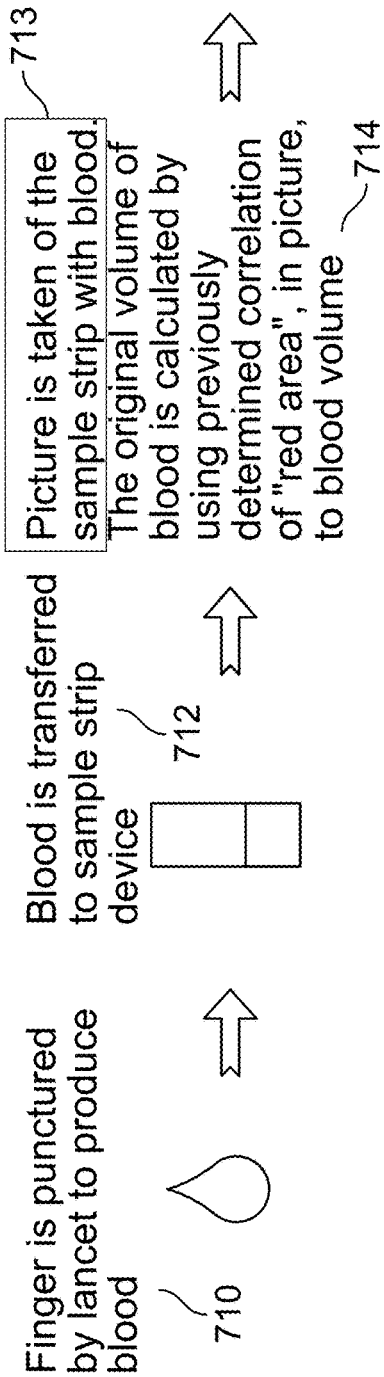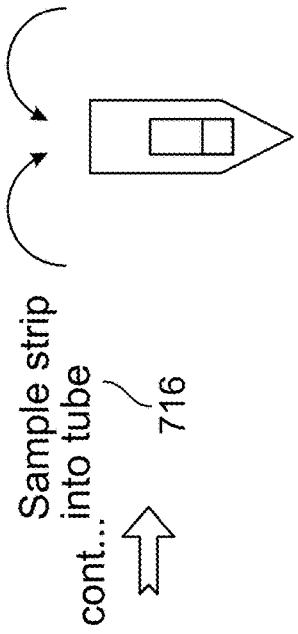
FIG. 7

FRONT SIDE          BACK SIDE

FLUID SAMPLING APPARATUS AND METHOD

CROSS-REFERENCE TO RELATED APPLICATION

This continuation-in-part application claims the benefit of U.S. patent application Ser. No. 14/216,761 filed 17 Mar. 2014. which in turn claims the benefit of U.S. provisional application No. 61/798,535, filed on 15 Mar. 2013, the contents of which are incorporated herein by reference. In addition, this continuation-in-part application claims the benefit of U.S. provisional application No. 62/634,344, filed on 23 Feb. 2018, the contents of which are incorporated herein by reference. A claim of priority is made.

TECHNICAL FIELD

Various embodiments described herein relate to a sampling apparatus and a method for bodily fluids, and, more specifically, a blood sampling apparatus and a method for using the same.

BACKGROUND

For many years, methods of testing for diseases, drugs and other antigens in humans have years been done using blood samples. These samples are collected in laboratories at the request of physicians. Generally, these tests require that blood is drawn by a trained phlebotomist is sent to a laboratory. Drawn blood is left in a test tube. These are relatively inefficient from the standpoint of shipping. Test tubes are also somewhat fragile. Shipping blood is also very time sensitive. The serum component of the blood, comprising a predominance of immunoglobulins, that contain antibodies to the disease or disease state in question, is tested using a variety of available test kits to assist in the diagnosis of various diseases including infectious diseases, cardiovascular diseases, cancers and many others. Such samples can also be tested for the presence of non-disease analytes such as metals, minerals, DNA, bacteria and organic molecules among others.

Another type of test is dried blood testing. This is called dry bloodspot sampling. In 1963, Robert Guthrie developed dried blood spot sampling for neonatal screening of metabolic disorders. Dried-blood-spot-cards are sometimes referred to as "Guthrie Cards". Dry bloodspot sampling has been successful for facilitating neonatal screening, home testing and remote site sampling collection and transport of samples to a laboratory for analysis. In the past, a puncture site is produced on the patient to produce blood. Drops of blood are placed onto a card with a particular type of paper or other suitable absorbent material. This method is difficult for patients to use. In order to eliminate or prevent contamination, the patient can not touch the card. The protocol for taking the sample requires the patient to form a droplet large enough so that it falls onto the absorbent material. This requires a fairly large amount of blood and also is very inconvenient for the patient. If a patient happens to be squeamish about the sight of blood, the test can be that much more difficult to perform. Once the sample is taken it is shipped to a lab. In order for the lab to standardize the size of the sample, the absorbent material is punched with a hole punch in the area of the containing the dried blood spot. The punch out is the portion of the taken sample that is used for testing. There are also on-line liquid extractions devices that fix the sample size to a standard amount by passing liquid through a fixed area of the dried blood spot.

Among the disadvantages of the dried blood spot card system, are:

1) The current system requires much more blood than is often required for the analytical procedure which results in a requirement of a larger lancet gauge and ultimately more pain for the subject being tested. Standard procedures for the current system result in spots that contain approximately 80 uL of blood. For analysis methods such as DNA sequencing and LC/MS, liquid chromatography/mass spectrometry, analysis this amount of blood is orders of magnitude more than what is required and many standard protocols simply dilute the sample prior to sample analysis.

2) The current system, specifically the card format of the system, is difficult to automate for a high throughput robotic scheme. The two-dimensional nature of these cards result in inherent difficulties in grasping and manipulating these cards in a high precision manner.

3) The current system makes a multisolvent or multi stage extraction protocol very difficult to accomplish. This is especial the case when the multisolvent/multistate protocol is meant to be automated.

4) Still another disadvantage of the blood spot cards, when prepared by the punch method or online methods, is that only a subset of the entire spot is used. This is problematic since the entire blood spot area is not homogenous, as can easily be determined by simple visual inspection by noticing that the edges of the spot appear darker than the center. Chemical analysis of various regions of a single spot does result in differential chemical composition of the multitude of sample areas.

5) Still another disadvantage of the current system is that the entire area of the card is exposed to the environment and therefore the potential for contamination on the card is highly probable.

6) In the current system, the original volume of the blood sample is not known. Assumptions are required in the preparation of the sample for analysis rather than simply having a known starting volume There exists an increasing demand for home blood sampling. To serve this demand, new blood collection devices must be developed. These blood collection devices should 1) be user friendly to allow a blood donor to collect their blood without assistance of another individual, 2) be relatively pain free, 3) deliver the blood sample, in satisfactory condition, to the blood testing laboratory 4) generate important information regarding characteristics of the specimen and specimen collection, be amenable to automated shipping and specimen processing and 6) allow for the identity authentication of the blood donor.

Dried-blood-spot (DBS) sampling cards are a proven type of blood collection device that are both easy to use and relatively pain free. These have been commonly used for decades in the newborn screening program. DBS sampling requires less blood which is an advantage compared to traditional blood draws. Typically, a lancet is used to prick the finger or heel thus producing a. droplet of blood that falls onto the paper card. The paper card, with the spot of blood on it, is allowed to dry producing a dried-blood-spot (DBS) specimen. Once the DBS specimen is dried, it can be stored at room temperature and shipped to a laboratory for analysis via common postal and shipping services.

Despite the advantages of DPS sampling, the most accurate blood testing results occur when trained professionals assist in the blood collection process. This is the case as deleterious aspects of the DBS blood collection process are minimized by performing the blood collection in a controlled environment such as a hospital by trained professionals. Therefore, when untrained individuals collect blood at home or other uncontrolled environments, undesirable aspects of the blood collection process might occur which can produce a less accurate and sometimes incorrect blood test result.

To overcome these blood collection challenges with regard to DBS blood sampling, elements of the DBS sampling device should exist to record the environmental conditions (temperature, humidity, atmospheric pressure, luminosity) of the uncontrolled environment along with the environmental conditions from the blood-collection-time until the sample arrives at the authorized blood testing laboratory. Knowledge of these environmental conditions could be used by trained professionals to inform aspects of the sample preparation and analysis with the ultimate goal of improving the values produced by the blood test.

Another consideration is the well documented "hematocrit problem" or "hematocrit effect" which causes inconsistent measurements across the blood hematocrit range for DBS based blood testing. Knowledge of the blood viscosity, or blood hematocrit, or a property of the sample that is related to blood viscosity or blood hematocrit, would allow for a "blood hematocrit correction" or "blood viscosity correction" as a means to improve the accuracy of lab tests. Therefore, elements of the DBS sampling device could exist to measure and record specific physical aspects of the dried blood spot sample including the 1) viscosity of the blood as it is absorbed onto the paper, 2) the infrared and visible absorbance/reflectance characteristics of the freshly collected blood spot, 3) the drying characteristics of the blood spot, and 4) the electrical properties (inductance, capacitance, resistance, conductance to name a few) of the blood spot. Knowledge of these DBS sample characteristics could be used by trained professionals to inform aspects of the sample preparation and analysis with the ultimate goal of improving the values produced by the blood test.

Furthermore, elements of the DBS sampling device should exist o authenticate the identity of the blood donor, the physical address or geolocation of the blood collection site, and the precise moment in time when the blood collection occurred. Consider the case of illicit drug testing, the authentication scheme has to be designed to eliminate individuals from "tricking" the process by using someone else's blood to produce a "clean" or drug free blood sample.

BRIEF DESCRIPTION OF THE DRAWINGS

The embodiments will be readily understood by the following detailed description in conjunction with the accompanying drawings, wherein like reference numerals designate like structural elements, and in which:

FIG. 2 is an exploded perspective view of a sample collection device used as part of the sample collection system, according to an example embodiment.

FIG. 3 is a perspective view of the sample collection device as assembled and ready for use, according to an example embodiment.

FIG. 7 is another flow diagram of a system for determining an amount of volume of blood based on an observed area of blood on the absorbent material, and analyzing the sample, according to an example embodiment.

FIG. 26 FIG. 10 was produced by finding the peak top position of the 2nd derivative of the conductance drying curve, according to an example embodiment.

DETAILED DESCRIPTION

In the following paper, numerous specific details are set forth to provide a thorough understanding of the concepts underlying the described embodiments. It will be apparent, however, to one skilled in the art that the described embodiments may be practiced without some or all of these specific details. In other instances, well known process steps have not been described in detail in order to avoid unnecessarily obscuring the underlying concepts.

Figure 1:
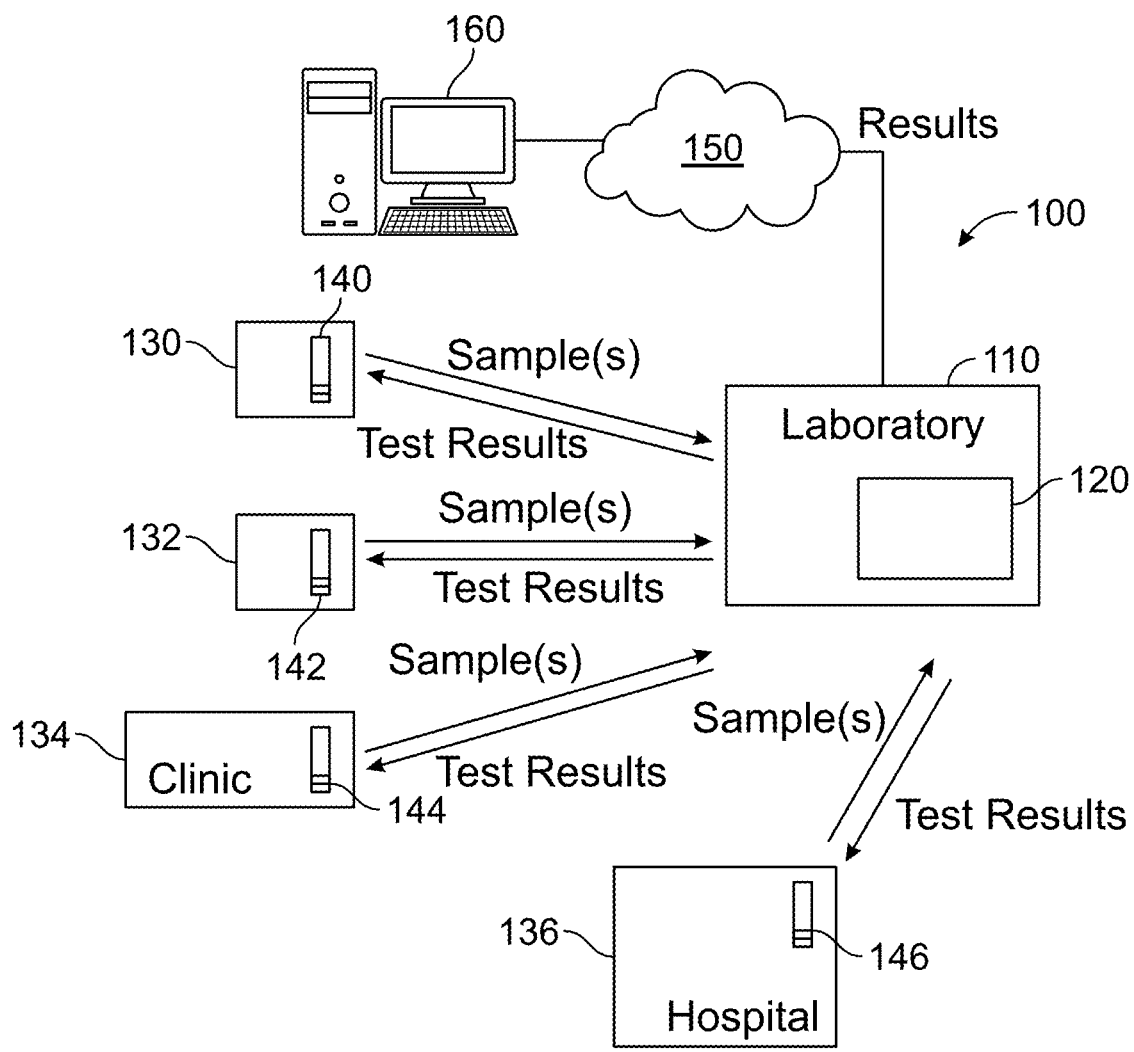
FIG. 1 is a schematic view of a sample collection system, according to an example embodiment.

FIG. 1 is a schematic view of a sample collection system 100, according to an example embodiment. The sample collection system 100 is a broad overview of how samples are collected and analyzed. The sample collection system 100 includes a laboratory 110 which includes an analysis portion 120. The system also includes a number of sites 130, 132, 134 and 136. The sites 130, 132, 134 136 can include individual doctor's offices, clinics, hospitals, households, membership gyms, retail stores, pharmacies, remote sampling sites any other facilities. At these various sites 130, 132, 134 and 136, blood samples are taken. As shown in FIG. 1, the blood samples 140, 142, 144, 146 are dried blood samples taken on a specific strip of absorbent material typically of cellulous or non-cellulous nature, and will be further described as part of this invention. The blood samples 140, 142, 144, 146 are sent to the lab or laboratory 110 where they are processed and analyzed. The analysis is conducted in the analysis portion 120. In one embodiment the analysis portion includes a liquid chromatogram/mass spectrometer system. In some embodiments the analysis and processing can be robotically controlled or otherwise automated. In other embodiments, the analysis and processing can be substantially automated or robotically controlled. In still other embodiments at least a portion of the analysis of process can be automated. Once the analysis is conducted test results are sent back to the various testing sites 130, 132, 134, 136 for discussions with patients regarding the results. Of course, the test results are correlated to the patient from whom a particular sample was taken. In one embodiment, the system 100 also includes a secure connection to the world wide web 150. A secure website hosted at the laboratory 110, or within a server on the cloud 150 can be used to transfer results to patients. A physician and patient or other health care professional can then discuss the results through one or more portals, such as a computer or computers, attached to the world wide web.

FIG. 2 is an exploded perspective view of a sample collection device 200 used as part of the sample collection system, according to an example embodiment. FIG. 3 is a perspective view of the sample collection device 200 as assembled and ready for use, according to an example embodiment. Now referring to both FIGS. 2 and 3, the sample collection device 200 will be further detailed. The sample collection device 200 includes a piece of absorbent material or absorbent material 210. In one particular embodiment the absorbent material is Whatman 903 paper available from GE Healthcare Bio-Sciences Corp. of Piscataway, N.J. 08855-1327 USA. In another embodiment, a non-cellulose material is the Agilent DMS material, 5301 Stevens Creek Blvd Santa Clara Calif. 95051 United States. As shown in FIGS. 2 and 3, absorbent material is cut to a specific size. Generally, the size the absorbent material will be uniform, in one embodiment. The sample collection device 200 also includes a handle 220, a cap 230, and a stem 240. The stem 240 attaches the absorbent material 210 to the cap 230. The handle 220 is attached to the cap 230. The stem 240 is made of a material capable of holding the absorbent material 210. The stem 240 is also made of a material that will not react or contaminate with any solvent used to extract the sample from the absorbent material 210. In one embodiment, the stem 240 is formed of stainless steel. The stem 240, in one embodiment, has the dimensions similar to a sewing needle. It should be understood that the stem can be made of other nonreactive materials, and that the dimensions of both the stem and the absorbent material 210 can be changed or different and still be within the scope of the invention.

The collection device 200 also includes a housing or clear container 250. The housing 250 includes a first open end 252 and a second open end 254. The first open end 252 is sized to allow the absorbent material 210 and the stem 240 to pass through the first opening 252 and into the main body of the housing 250. The first open end 252 captures or catches the cap 230. The cap 230 fits within the open end 252 and also acts as a stop so that the absorbent material 210 is positioned near or proximate the second open end 254. The housing 250 allows the sample device 200 to be handled without significant contamination of the absorbent material 210. In addition the housing or clear container 250 also protects the stem 240 and the absorbent material 210. The handle 220 allows for automatic processing of the sample contained within the absorbent material 210 attached to the handle 220 via the cap 230 and the stem 240. In one embodiment a robot can be used to identify the specific device 200 among many devices 200 by virtue of an identification marker or identifier, such as a barcode or QR code or similar marker, contained on the handle 220. The marker can be read by a reader. The robot includes a mechanism to grab the handle 220 and move the attached cap 230, stem 240 and absorbent material 210 to various stations where the sample on the absorbent material 210 is processed and analyzed.

In another embodiment, a barcode can be provided on the specific device at the time of manufacture. The barcode would be unique. At the time of taking or submitting the sample, the patient could be linked to the unique barcode identifier.

Figure 4:
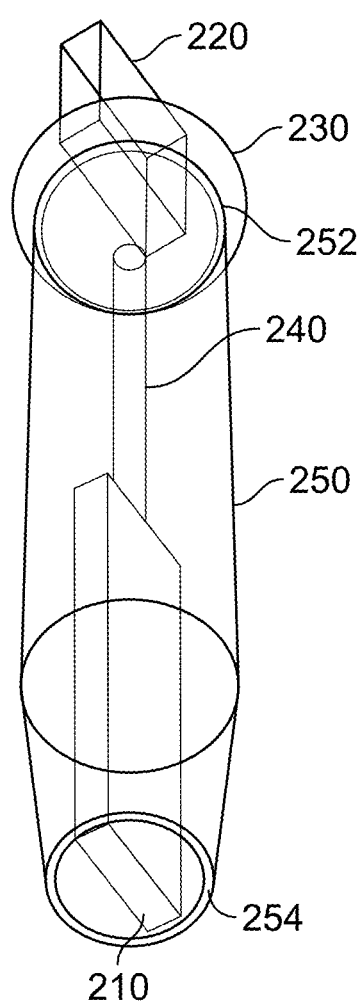
FIG. 4 is a bottom perspective view of the sample collection device as assembled and ready for use, according to an example embodiment.

FIG. 4 is a bottom perspective view of the sample collection device as assembled and ready for use, according to an example embodiment. FIGS. 3 and 4 show the sample collection device 200 in an assembled form and ready for taking a sample. FIG. 4 shows the position of the absorbent material near the second opening 254 of the housing or clear container 250.

In operation, when a sample is collected or taken it is much easier on a patient. The patient's finger or other body portion is lanced to produce a source of blood for the sample. The sampling device 200 is moved into close proximity to the blood at the lance site. The absorbent material touches the blood at the Lance site, and blood is absorbed into the absorbent material 210. The sampling device is then removed and placed into a holder for a number of the sample devices. The same lance site can then be used to collect another sample with a fresh sampling device 200. In this way it is easier on the patient. The patient merely has to be pricked or lanced one time and multiple samples can be obtained from the lance site. The patient also does not have to manipulate or otherwise squeeze the area around the lance site to produce enough blood for a sample. In addition, much less blood is needed to produce a number of samples. The process is faster and more efficient than previous ways of obtaining blood samples for blood spot tests.

After a blood sample is transferred to the device 200 via the opening 254, the device 200 is placed in a holder. The absorbent paper 210 carrying the blood sample dries due to exposure to the surrounding environment. Generally, circulating air dries the blood on the absorbent material or absorbent paper. It should be noted that the blood sample is transferred to the device 200 and more specifically to the absorbent material without being touched by anyone. Therefore, the chance for contamination from such a source is minimized. In addition, the absorbent material is dimensioned to accommodate the widest blood volume range with the lowest sample dilution amount so that testing result can be accurate through a wide range of values. It has been found that an amount of blood in a sample should be in the range of 2-15 microliters. For consistency in conducting a blood test, it is desirable to substantially cover or totally cover the absorbent material. If the material is too long, too much solvent is needed to completely cover or substantially completely cover the absorbent material. Table 1 below shows dimensions which absorb 15 microliters of blood or more. The absorbent material having dimensions which absorb more than 15 microliters of blood are considered too large.

Table 2 shows the dimensions of the absorbent material where the least amount of solvent is required for a given condition where at least 2 microliters of blood are on or dried onto the absorbent material.

Table 3 shows the dimensions of the absorbent material where the sample includes at least 2-15 microliters of blood or dried blood and where the least amount of solvent is required to cover or substantially cover the absorbent material. Of course, this example is for blood or dried blood. If different materials were being tested, these dimensions could change. In other words, Table 3 shows the intersection of Tables 1 and 2.

Table 1 shows the maximum Strip capacity of Blood (micro liters) for given strip dimensions. This table only shows values that are equal to or greater than 15 uL and this is defined as "condition 1".

TABLE 1

| | | Strip Width (mm) | | | | | | | | | | | | | | | |
|---|---|---|---|---|---|---|---|---|---|---|---|---|---|---|---|---|---|
| | | 0.5 | 1.0 | 1.5 | 2.0 | 2.5 | 3.0 | 3.5 | 4.0 | 4.5 | 5.0 | 5.5 | 6.0 | 6.5 | 7.0 | 7.5 | 8.0 |
| Strip Height (mm) | 1 | | | | | | | | | | | | | | | | |
| | 2 | | | | | | | | | | | | | | | | |
| | 3 | | | | | | | | | | | | | | | | |
| | 4 | | | | | | | | | | | | | | | | |
| | 5 | | | | | | | | | | | | | | | | 15.3 |
| | 6 | | | | | | | | | | | | | | 16.1 | 17.3 | 18.4 |
| | 7 | | | | | | | | | | | | 16.1 | 17.5 | 18.8 | 20.2 | 21.6 |
| | 8 | | | | | | | | | | 15.3 | 16.9 | 18.4 | 20 | 21.6 | 23.2 | 24.8 |
| | 9 | | | | | | | | | 15.5 | 17.3 | 19 | 20.8 | 22.6 | 24.4 | 26.2 | 27.9 |
| | 10 | | | | | | | | 15.3 | 17.3 | 19.2 | 21.2 | 23.2 | 25.2 | 27.1 | 29.1 | 31.1 |
| | 11 | | | | | | | | 16.9 | 19 | 21.2 | 23.4 | 25.6 | 27.7 | 29.9 | 32.1 | 34.3 |
| | 12 | | | | | | | 16.1 | 18.4 | 20.8 | 23.2 | 25.6 | 27.9 | 30.3 | 32.7 | 35 | 37.4 |
| | 13 | | | | | | | 17.5 | 20 | 22.6 | 25.2 | 27.7 | 30.3 | 32.9 | 35.4 | 38 | 40.6 |
| | 14 | | | | | | 16.1 | 18.8 | 21.6 | 24.4 | 27.1 | 29.9 | 32.7 | 35.4 | 38.2 | 41 | 43.7 |
| | 15 | | | | | | 17.3 | 20.2 | 23.2 | 26.2 | 29.1 | 32.1 | 35 | 38 | 41 | 43.9 | 46.9 |
| | 16 | | | | | 15.3 | 18.4 | 21.6 | 24.8 | 27.9 | 31.1 | 34.3 | 37.4 | 40.6 | 43.7 | 46.9 | 50.1 |
| | 17 | | | | | 16.3 | 19.6 | 23 | 26.4 | 29.7 | 33.1 | 36.4 | 39.8 | 43.2 | 46.5 | 49.9 | 53.2 |
| | 18 | | | | | 17.3 | 20.8 | 24.4 | 27.9 | 31.5 | 35 | 38.6 | 42.2 | 45.7 | 49.3 | 52.8 | 56.4 |
| | 19 | | | | | 18.2 | 22 | 25.8 | 29.5 | 33.3 | 37 | 40.8 | 44.5 | 48.3 | 52 | 55.8 | 59.6 |
| | 20 | | | | 15.3 | 19.2 | 23.2 | 27.1 | 31.1 | 35 | 39 | 43 | 46.9 | 50.9 | 54.8 | 58.8 | 62.7 |
| | 21 | | | | 16.1 | 20.2 | 24.4 | 28.5 | 32.7 | 36.8 | 41 | 45.1 | 49.3 | 53.4 | 57.6 | 61.7 | 65.9 |
| | 22 | | | | 16.9 | 21.2 | 25.6 | 29.9 | 34.3 | 38.6 | 43 | 47.3 | 51.7 | 56 | 60.3 | 64.7 | 69 |
| | 23 | | | | 17.7 | 22.2 | 26.7 | 31.3 | 35.8 | 40.4 | 44.9 | 49.5 | 54 | 58.6 | 63.1 | 67.7 | 72.2 |
| | 24 | | | | 18.4 | 23.2 | 27.9 | 32.7 | 37.4 | 42.2 | 46.9 | 51.7 | 56.4 | 61.1 | 65.9 | 70.6 | 75.4 |
| | 25 | | | | 19.2 | 24.2 | 29.1 | 34.1 | 39 | 43.9 | 48.9 | 53.8 | 58.8 | 63.7 | 68.7 | 73.6 | 78.5 |
| | 26 | | | | 20 | 25.2 | 30.3 | 35.4 | 40.6 | 45.7 | 50.9 | 56 | 61.1 | 66.3 | 71.4 | 76.6 | 81.7 |
| | 27 | | | 15.5 | 20.8 | 26.2 | 31.5 | 36.8 | 42.2 | 47.5 | 52.8 | 58.2 | 63.5 | 68.8 | 74.2 | 79.5 | 84.9 |
| | 28 | | | 16.1 | 21.6 | 27.1 | 32.7 | 38.2 | 43.7 | 49.3 | 54.8 | 60.3 | 65.9 | 71.4 | 77 | 82.5 | 88 |
| | 29 | | | 16.7 | 22.4 | 28.1 | 33.9 | 39.6 | 45.3 | 51.1 | 56.8 | 62.5 | 68.3 | 74 | 79.7 | 85.5 | 91.2 |
| | 30 | | | 17.3 | 23.2 | 29.1 | 35 | 41 | 46.9 | 52.8 | 58.8 | 64.7 | 70.6 | 76.6 | 82.5 | 88.4 | 94.3 |
| | 31 | | | 17.9 | 24 | 30.1 | 36.2 | 42.4 | 48.5 | 54.6 | 60.7 | 66.9 | 73 | 79.1 | 85.3 | 91.4 | 97.5 |
| | 32 | | | 18.4 | 24.8 | 31.1 | 37.4 | 43.7 | 50.1 | 56.4 | 62.7 | 69 | 75.4 | 81.7 | 88 | 94.3 | 101 |
| | 33 | | | 19 | 25.6 | 32.1 | 38.6 | 45.1 | 51.7 | 58.2 | 64.7 | 71.2 | 77.7 | 84.3 | 90.8 | 97.3 | 104 |
| | 34 | | | 19.6 | 26.4 | 33.1 | 39.8 | 46.5 | 53.2 | 60 | 66.7 | 73.4 | 80.1 | 86.8 | 93.6 | 100 | 107 |
| | 35 | | | 20.2 | 27.1 | 34.1 | 41 | 47.9 | 54.8 | 61.7 | 68.7 | 75.6 | 82.5 | 89.4 | 96.3 | 103 | 110 |
| | 36 | | | 20.8 | 27.9 | 35 | 42.2 | 49.3 | 56.4 | 63.5 | 70.6 | 77.7 | 84.9 | 92 | 99.1 | 106 | 113 |
| | 37 | | | 21.4 | 28.7 | 36 | 43.4 | 50.7 | 58 | 65.3 | 72.6 | 79.9 | 87.2 | 94.5 | 102 | 109 | 117 |

TABLE 1-continued

| | Strip Width (mm) | | | | | | | | | | | | | | | |
|---|---|---|---|---|---|---|---|---|---|---|---|---|---|---|---|---|
| | 0.5 | 1.0 | 1.5 | 2.0 | 2.5 | 3.0 | 3.5 | 4.0 | 4.5 | 5.0 | 5.5 | 6.0 | 6.5 | 7.0 | 7.5 | 8.0 |
| 38 | | 22 | 29.5 | 37 | 44.5 | 52 | 59.6 | 67.1 | 74.6 | 82.1 | 89.6 | 97.1 | 105 | 112 | 120 | |
| 39 | | 22.6 | 30.3 | 38 | 45.7 | 53.4 | 61.1 | 68.8 | 76.6 | 84.3 | 92 | 99.7 | 107 | 115 | 123 | |
| 40 | 15.3 | 23.2 | 31.1 | 39 | 46.9 | 54.8 | 62.7 | 70.6 | 78.5 | 86.4 | 94.3 | 102 | 110 | 118 | 126 | |
| 41 | 15.7 | 23.8 | 31.9 | 40 | 48.1 | 56.2 | 64.3 | 72.4 | 80.5 | 88.6 | 96.7 | 105 | 113 | 121 | 129 | |
| 42 | 16.1 | 24.4 | 32.7 | 41 | 49.3 | 57.6 | 65.9 | 74.2 | 82.5 | 90.8 | 99.1 | 107 | 116 | 124 | 132 | |
| 43 | 16.5 | 25 | 33.5 | 42 | 50.5 | 59 | 67.5 | 76 | 84.5 | 93 | 102 | 110 | 119 | 127 | 136 | |
| 44 | 16.9 | 25.6 | 34.3 | 43 | 51.7 | 60.3 | 69 | 77.7 | 86.4 | 95.1 | 104 | 113 | 121 | 130 | 139 | |
| 45 | 17.3 | 26.2 | 35 | 43.9 | 52.8 | 61.7 | 70.6 | 79.5 | 88.4 | 97.3 | 106 | 115 | 124 | 133 | 142 | |
| 46 | 17.7 | 26.7 | 35.8 | 44.9 | 54 | 63.1 | 72.2 | 81.3 | 90.4 | 99.5 | 109 | 118 | 127 | 136 | 145 | |
| 47 | 18.1 | 27.3 | 36.6 | 45.9 | 55.2 | 64.5 | 73.8 | 83.1 | 92.4 | 102 | 111 | 120 | 130 | 139 | 148 | |
| 48 | 18.4 | 27.9 | 37.4 | 46.9 | 56.4 | 65.9 | 75.4 | 84.9 | 94.3 | 104 | 113 | 123 | 132 | 142 | 151 | |
| 49 | 18.8 | 28.5 | 38.2 | 47.9 | 57.6 | 67.3 | 77 | 86.6 | 96.3 | 106 | 116 | 125 | 135 | 145 | 154 | |
| 50 | 19.2 | 29.1 | 39 | 48.9 | 58.8 | 68.7 | 78.5 | 88.4 | 98.3 | 108 | 118 | 128 | 138 | 148 | 158 | |

Table 2 shows sample dilutions at given strip dimensions assuming a min of 2 uL blood on strip and 100% of strip covered with extraction solvent. This assumes the strip is placed at the bottom of a vial and the vial has an internal dimension of the strip width plus 2 mm. The additional 2 mm allows for movement of the strip in and out of the vial. This table only shows the lowest 20% dilution results and is defined as "condition 2".

TABLE 2

| | | Strip Width (mm) | | | | | | | | | | | | | | | |
|---|---|---|---|---|---|---|---|---|---|---|---|---|---|---|---|---|---|
| | | 0.5 | 1 | 1.5 | 2 | 2.5 | 3 | 3.5 | 4 | 4.5 | 5 | 5.5 | 6 | 6.5 | 7 | 7.5 | 8 |
| Strip Height (mm) | 1 | 7.5 | 10 | 12.5 | 15 | 17.5 | 20 | 22.5 | 25 | 27.5 | 30 | 32.5 | 35 | 37.5 | 40 | 42.5 | 45 |
| | 2 | 15 | 20 | 25 | 30 | 35 | 40 | 45 | 50 | 55 | 60 | 65 | 70 | 75 | 80 | 85 | 90 |
| | 3 | 22.5 | 30 | 37.5 | 45 | 52.5 | 60 | 67.5 | 75 | 82.5 | 90 | 97.5 | 105 | 113 | 120 | 128 | 135 |
| | 4 | 30 | 40 | 50 | 60 | 70 | 80 | 90 | 100 | 110 | 120 | 130 | 140 | 150 | 160 | 170 | 180 |
| | 5 | 37.5 | 50 | 62.5 | 75 | 87.5 | 100 | 113 | 125 | 138 | 150 | 163 | 175 | 188 | 200 | 213 | 225 |
| | 6 | 45 | 60 | 75 | 90 | 105 | 120 | 135 | 150 | 165 | 180 | 195 | 210 | 225 | 240 | 255 | 270 |
| | 7 | 52.5 | 70 | 87.5 | 105 | 123 | 140 | 158 | 175 | 193 | 210 | 228 | 245 | 263 | 280 | 298 | 315 |
| | 8 | 60 | 80 | 100 | 120 | 140 | 160 | 180 | 200 | 220 | 240 | 260 | 280 | 300 | 320 | 340 | 360 |
| | 9 | 67.5 | 90 | 113 | 135 | 158 | 180 | 203 | 225 | 248 | 270 | 293 | 315 | 338 | 360 | 383 | 405 |
| | 10 | 75 | 100 | 125 | 150 | 175 | 200 | 225 | 250 | 275 | 300 | 325 | 350 | 375 | 400 | 425 | 450 |
| | 11 | 82.5 | 110 | 138 | 165 | 193 | 220 | 248 | 275 | 303 | 330 | 358 | 385 | 413 | 440 | | |
| | 12 | 90 | 120 | 150 | 180 | 210 | 240 | 270 | 300 | 330 | 360 | 390 | 420 | 450 | | | |
| | 13 | 97.5 | 130 | 163 | 195 | 228 | 260 | 293 | 325 | 358 | 390 | 423 | 455 | | | | |
| | 14 | 105 | 140 | 175 | 210 | 245 | 280 | 315 | 350 | 385 | 420 | 455 | | | | | |
| | 15 | 113 | 150 | 188 | 225 | 263 | 300 | 338 | 375 | 413 | 450 | | | | | | |
| | 16 | 120 | 160 | 200 | 240 | 280 | 320 | 360 | 400 | 440 | | | | | | | |
| | 17 | 128 | 170 | 213 | 255 | 298 | 340 | 383 | 425 | | | | | | | | |
| | 18 | 135 | 180 | 225 | 270 | 315 | 360 | 405 | 450 | | | | | | | | |
| | 19 | 143 | 190 | 238 | 285 | 333 | 380 | 428 | | | | | | | | | |
| | 20 | 150 | 200 | 250 | 300 | 350 | 400 | 450 | | | | | | | | | |
| | 21 | 158 | 210 | 263 | 315 | 368 | 420 | | | | | | | | | | |
| | 22 | 165 | 220 | 275 | 330 | 385 | 440 | | | | | | | | | | |
| | 23 | 173 | 230 | 288 | 345 | 403 | | | | | | | | | | | |
| | 24 | 180 | 240 | 300 | 360 | 420 | | | | | | | | | | | |
| | 25 | 188 | 250 | 313 | 375 | 438 | | | | | | | | | | | |
| | 26 | 195 | 260 | 325 | 390 | 455 | | | | | | | | | | | |
| | 27 | 203 | 270 | 338 | 405 | | | | | | | | | | | | |
| | 28 | 210 | 280 | 350 | 420 | | | | | | | | | | | | |
| | 29 | 218 | 290 | 363 | 435 | | | | | | | | | | | | |
| | 30 | 225 | 300 | 375 | 450 | | | | | | | | | | | | |
| | 31 | 233 | 310 | 388 | | | | | | | | | | | | | |
| | 32 | 240 | 320 | 400 | | | | | | | | | | | | | |
| | 33 | 248 | 330 | 413 | | | | | | | | | | | | | |
| | 34 | 255 | 340 | 425 | | | | | | | | | | | | | |
| | 35 | 263 | 350 | 438 | | | | | | | | | | | | | |
| | 36 | 270 | 360 | 450 | | | | | | | | | | | | | |
| | 37 | 278 | 370 | | | | | | | | | | | | | | |
| | 38 | 285 | 380 | | | | | | | | | | | | | | |
| | 39 | 293 | 390 | | | | | | | | | | | | | | |
| | 40 | 300 | 400 | | | | | | | | | | | | | | |
| | 41 | 308 | 410 | | | | | | | | | | | | | | |
| | 42 | 315 | 420 | | | | | | | | | | | | | | |
| | 43 | 323 | 430 | | | | | | | | | | | | | | |
| | 44 | 330 | 440 | | | | | | | | | | | | | | |
| | 45 | 338 | 450 | | | | | | | | | | | | | | |
| | 46 | 345 | | | | | | | | | | | | | | | |
| | 47 | 353 | | | | | | | | | | | | | | | |
| | 48 | 360 | | | | | | | | | | | | | | | |

TABLE 2-continued

| | Strip Width (mm) | | | | | | | | | | | | | | | |
|---|---|---|---|---|---|---|---|---|---|---|---|---|---|---|---|---|
| | 0.5 | 1 | 1.5 | 2 | 2.5 | 3 | 3.5 | 4 | 4.5 | 5 | 5.5 | 6 | 6.5 | 7 | 7.5 | 8 |
| 49 | 368 | | | | | | | | | | | | | | | |
| 50 | 375 | | | | | | | | | | | | | | | |

Table 3 shows the strip dimension combinations where "condition 1" and "condition 2" are both satisfied and where the width is greater than the height. A value of "1", indicates where these conditions are satisfied.

TABLE 3

| | | Strip Width (mm) | | | | | | | | | | | | | | | |
|---|---|---|---|---|---|---|---|---|---|---|---|---|---|---|---|---|---|
| | | 0.5 | 1 | 1.5 | 2 | 2.5 | 3 | 3.5 | 4 | 4.5 | 5 | 5.5 | 6 | 6.5 | 7 | 7.5 | 8 |
| Strip Height (mm) | 1 | | | | | | | | | | | | | | | | |
| | 2 | | | | | | | | | | | | | | | | |
| | 3 | | | | | | | | | | | | | | | | |
| | 4 | | | | | | | | | | | | | | | | |
| | 5 | | | | | | | | | | | | | | | 1 | |
| | 6 | | | | | | | | | | | | | 1 | 1 | 1 | |
| | 7 | | | | | | | | | | | 1 | 1 | 1 | 1 | 1 | |
| | 8 | | | | | | | | | 1 | 1 | 1 | 1 | 1 | 1 | 1 | |
| | 9 | | | | | | | | 1 | 1 | 1 | 1 | 1 | 1 | 1 | 1 | |
| | 10 | | | | | | | 1 | 1 | 1 | 1 | 1 | 1 | 1 | 1 | 1 | |
| | 11 | | | | | | | 1 | 1 | 1 | 1 | 1 | 1 | 1 | | | |
| | 12 | | | | | | 1 | 1 | 1 | 1 | 1 | 1 | 1 | | | | |
| | 13 | | | | | | 1 | 1 | 1 | 1 | 1 | 1 | | | | | |
| | 14 | | | | | 1 | 1 | 1 | 1 | 1 | 1 | | | | | | |
| | 15 | | | | | 1 | 1 | 1 | 1 | 1 | | | | | | | |
| | 16 | | | | 1 | 1 | 1 | 1 | 1 | | | | | | | | |
| | 17 | | | | 1 | 1 | 1 | 1 | | | | | | | | | |
| | 18 | | | | 1 | 1 | 1 | 1 | | | | | | | | | |
| | 19 | | | | 1 | 1 | 1 | | | | | | | | | | |
| | 20 | | | 1 | 1 | 1 | 1 | | | | | | | | | | |
| | 21 | | | 1 | 1 | 1 | | | | | | | | | | | |
| | 22 | | | 1 | 1 | 1 | | | | | | | | | | | |
| | 23 | | | 1 | 1 | | | | | | | | | | | | |
| | 24 | | | 1 | 1 | | | | | | | | | | | | |
| | 25 | | | 1 | 1 | | | | | | | | | | | | |
| | 26 | | | 1 | 1 | | | | | | | | | | | | |
| | 27 | | 1 | 1 | | | | | | | | | | | | | |
| | 28 | | 1 | 1 | | | | | | | | | | | | | |
| | 29 | | 1 | 1 | | | | | | | | | | | | | |
| | 30 | | 1 | 1 | | | | | | | | | | | | | |
| | 31 | | 1 | | | | | | | | | | | | | | |
| | 32 | | 1 | | | | | | | | | | | | | | |
| | 33 | | 1 | | | | | | | | | | | | | | |
| | 34 | | 1 | | | | | | | | | | | | | | |
| | 35 | | 1 | | | | | | | | | | | | | | |
| | 36 | | 1 | | | | | | | | | | | | | | |
| | 37 | | | | | | | | | | | | | | | | |
| | 38 | | | | | | | | | | | | | | | | |
| | 39 | | | | | | | | | | | | | | | | |
| | 40 | 1 | | | | | | | | | | | | | | | |
| | 41 | 1 | | | | | | | | | | | | | | | |
| | 42 | 1 | | | | | | | | | | | | | | | |
| | 43 | 1 | | | | | | | | | | | | | | | |
| | 44 | 1 | | | | | | | | | | | | | | | |
| | 45 | 1 | | | | | | | | | | | | | | | |
| | 46 | | | | | | | | | | | | | | | | |
| | 47 | | | | | | | | | | | | | | | | |
| | 48 | | | | | | | | | | | | | | | | |
| | 49 | | | | | | | | | | | | | | | | |
| | 50 | | | | | | | | | | | | | | | | |

Once the sample is obtained in the blood sampling device 200, the blood sampling device can be shipped to a lab 110 for further processing and analysis. The blood and the blood sampling device 200 dries so this test or sampling device is easier to transport. In addition the sampling device 200 is also more durable and tough so that it can withstand shipping to the laboratory 110. It should be noted, that in some example embodiments, a cover (not shown) may be placed on the second end 252 of the container or housing 250 during transport. This would further protect the absorbent material 210 during transport and would also reduce contamination to the absorbent material 210. Furthermore a drying device such as silica gel may be contained in the cover to further aid in sample dehydration during the transportation and storage process. The drying device could also be used to keep the atmosphere within the shipping package dry during the shipping process.

Figure 5:
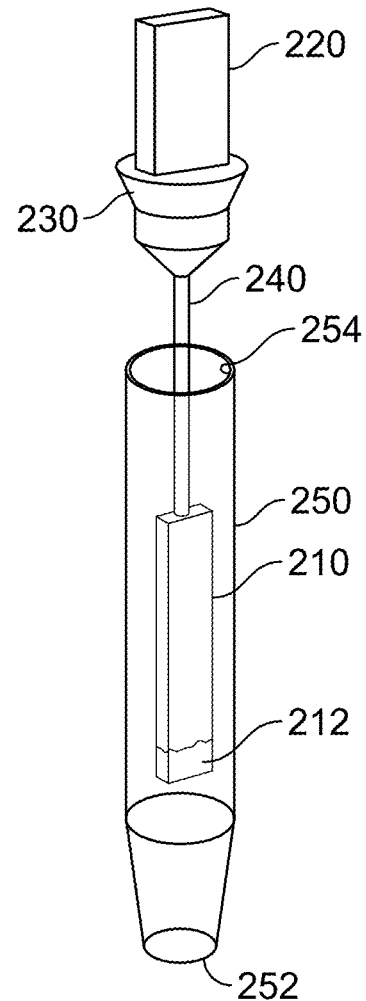
FIG. 5 is a perspective view of the sample collection device as the absorbent material is being removed from the housing at a testing site, according to an example embodiment.

FIG. 5 is a perspective view of the sample collection device as the absorbent material 210 is being removed from the housing at a laboratory 110, according to an example embodiment. More specifically the absorbent material 210, the stem 240, the cap 230 and the handle 220 are removed from the housing 250 at the laboratory 110. The handle 220 is sufficiently strong to allow a robot to pinch or grab the handle and move the sample 210. In some embodiments, it is contemplated that a robot could be configured that could grab or otherwise engage a plurality of handles 220. It should be noted that the absorbent paper 210 includes a dried blood portion 212 on the distal end of the absorbent material 210.

Figure 6:
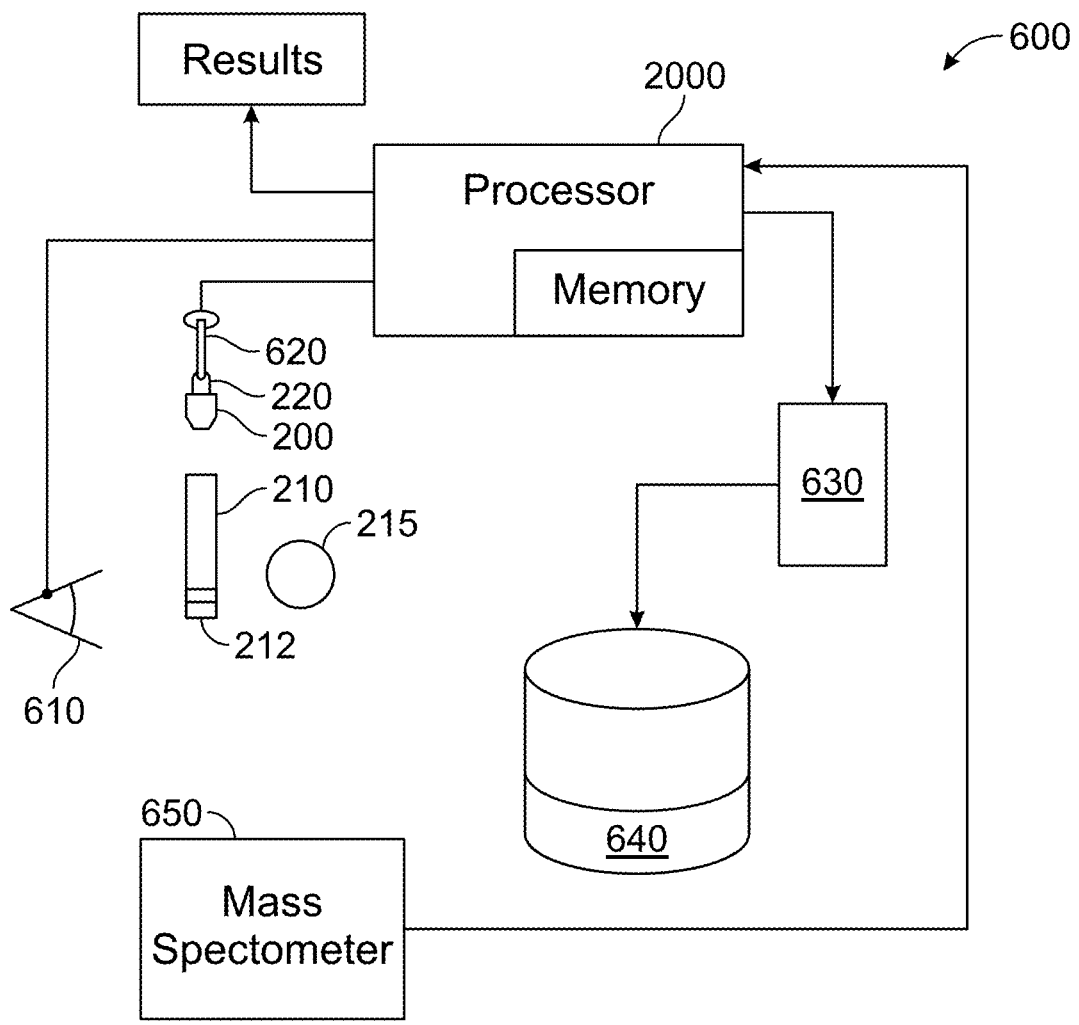
FIG. 6 is a flow diagram of a system for determining an amount of volume of blood based on an observed area of blood on the absorbent material, and analyzing the sample, according to an example embodiment.

FIG. 6 is a schematic diagram of a system 600 for analyzing a dried blood sample, according to an example embodiment. The system 600 includes an optic system 610 and a robot 620 for grabbing the handle 220 of a sampling device 200 and positioning the dried blood portion 212 of the absorbent material 210 before the optic system 610. The system 600 also includes a processor associated memory 2000, a source of solvent 630, a container for the solvent 640 and a liquid chromatogram/mass spectrometer system 650. In one embodiment the system could include an optical reference object 215 or area standard.

The absorbent material 210 has a set of dimensions. Given the set of dimensions, the area of the dried blood portion 212 can be determined by the optic system. In one example embodiment, the optic system is a camera which takes a picture of a particular absorbent material 210. The dimensions of the dried blood portion 212 can either be determined from the picture or can be known given that the dimensions of the absorbent material 210 are also known. Once the area of the dried blood portion 212 is determined, a table or a formula within the processor(s) 2000 and its associated memory can be used to determine or correlate area to a volume of blood associated with the dried blood portion 212 of the sample 210. This determination can be made by estimating the area or otherwise determining the size of the area and relating it to a table or formula to convert the area to a volume of blood. In one embodiment, the optical reference object 215 or area standard is included in the picture with the dried blood portion 212. The area reference standard 215 can then be used in a calculation to determine the absolute area of the dried blood portion 212.

The system 600 controls the amount of solvent placed in a solvent container 640. A source of solvent 630 is controlled by the processor 2000. Once the volume of blood is determined, and amount of solvent is placed into the solvent container 640 from the source of solvent 630. The exact amount of solvent is determined by the processor 2000. The processor controls the source of solvent 630 to place an amount of solvent into the solvent container 640. The robot 620, which is also owned under control of the processor, moves the absorbent material 210 into the solvent container 640. Once the absorbent material 210 has been in the solvent for a sufficient amount of time or once the extraction is complete, the solvent with the various blood compliments from the absorbent material 210 is placed into the liquid chromatograph/mass spectrometer platform 650 for analysis. In other example embodiments the solvent containing the extracted blood components can be further processed including, mixing with other extraction solvents, dilution procedures, concentration procedures, derivatization procedures and the like, prior to being placed into the liquid chromatograph/mass spectrometer platform 650 for analysis. In one example embodiment the solvent container 640 or extraction vial, where the extraction takes place, could be replaced with a fixed cavity physically connected to the robot 620. This cavity would be of similar dimensions to the solvent container 640 and would house the solvent and absorbent material 210 during the extraction. This cavity would eliminate the need for costly and disposable extraction vials 640.

FIG. 7 is a flow diagram of a system and method 700 for determining an amount of volume of blood based on an observed area of blood on the absorbent material, and analyzing the sample, according to an example embodiment. The method 700 includes initially puncturing the finger with a lancet to produce blood 710, and placing a sampling device near the blood to transfer blood to the sample strip device 712. The sample device is then sent to a laboratory where a picture is taken of the sample strip and the dried blood portion 713. From the picture, the original volume of blood is calculated using previously determined correlation of the blood-colored area of the picture to a blood volume 714. It should be noted that in some instances a formula can be used for a given determined area. In other words, the correlation of the blood-colored area in the picture does not have to be previously determined. The method 700 also includes placing a sample strip into a tube 716 and placing an amount of solvent related to the original blood volume into the tube 718. The strip or sample strip is then removed from the tube, leaving the solvent with dissolved blood components 719. The method also includes analyzing the solvent with liquid chromatography/mass spectrometry methods 720.

Figure 8:
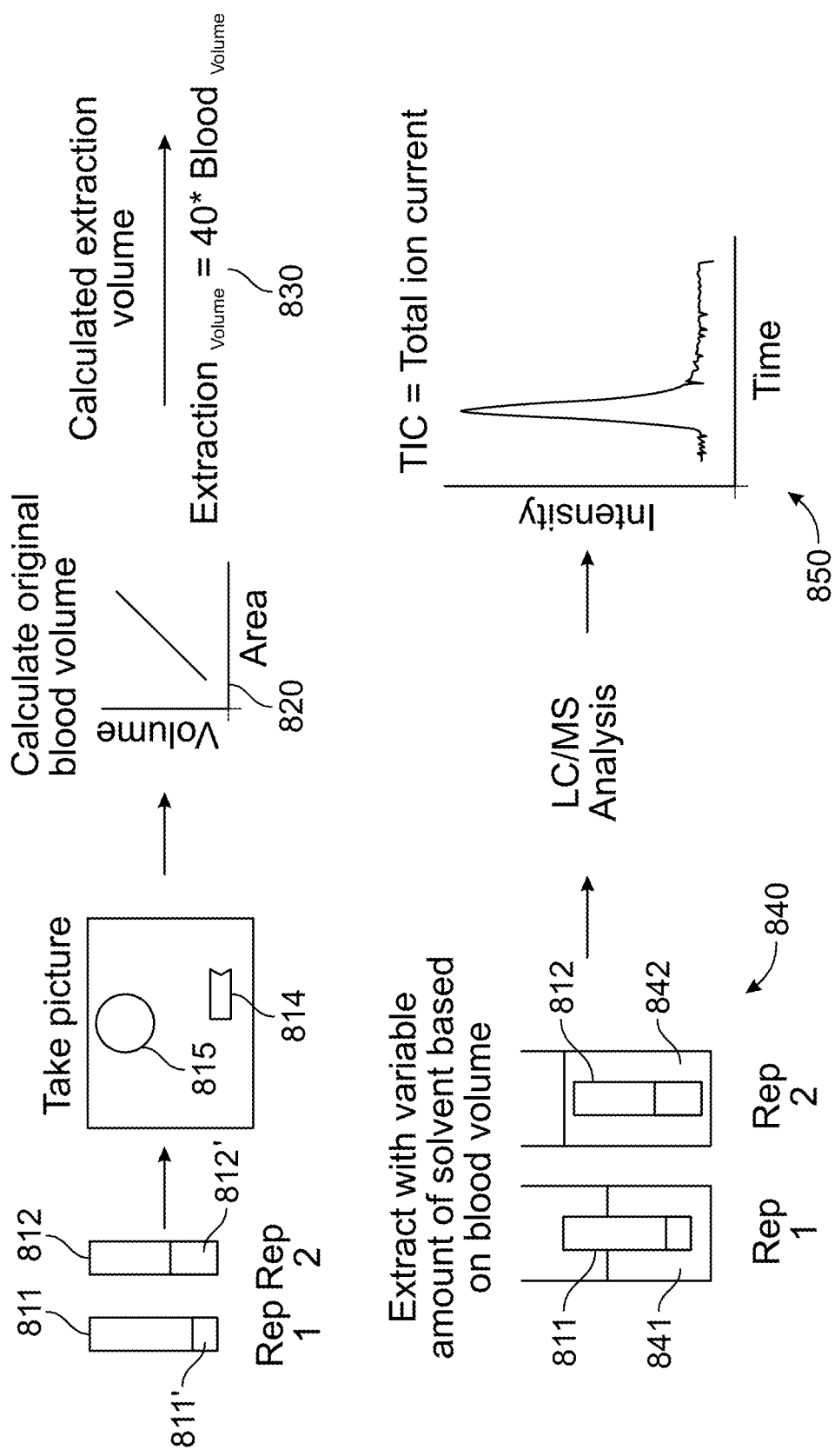
FIG. 8 is a schematic view of a computing system that can be used to control robots and conduct various aspects of the analyst, according to an example embodiment.

FIG. 8 is a schematic view of various portions of the system 600 that further details various aspects of the analysis, according to an example embodiment. As shown in FIG. 8, two test strips 811 and 812 are shown. The two test strips have different sizes or areas of dried blood portions 811' and 812'. A picture taken of both samples. As shown in FIG. 8, the dried blood sample is placed near a reference portion when the picture is taken. The amount of area of dried blood is determined from the picture taken.

In one embodiment, an area reference standard 815 is included in the picture with an example dried blood portion 814. This is used to in a calculation to convert a pixel count that corresponds to the dried blood portion 814 to an absolute area value.

As shown in FIG. 8 data table 820 or formula can be used to correlate the area of the dried blood sample portion 811', 812' to the volume of blood originally absorbed by the absorbent material. From the amount of area and the amount of volume and extraction volume for the solvent can be calculated or otherwise determined, as depicted by reference numeral 830. The samples 811, 812 are then placed in the respective extraction volumes for the samples. As shown by reference numeral 840, there is a lesser volume of solvent 841 for extraction of the components from the sample 811 then the volume of solvent 842 associated with sample 812. Basically, the amount of solvent used in each instance is proportional to the amount of dried blood on the sample 811, 812.

Now referring to 850 liquid chromatography/mass spectroscopy analysis are performed to produce a time versus intensity mapping of the total ion current. Features of the total ion current result from the solute contained in the sample solution. Of course before liquid chromatography/mass spectroscopy analysis the samples 811, 812 are removed from the sample solution 841, 842, respectively. The sample solutions 841 and 842 are what undergo liquid chromatography and mass spectroscopy analysis.

Figure 9:
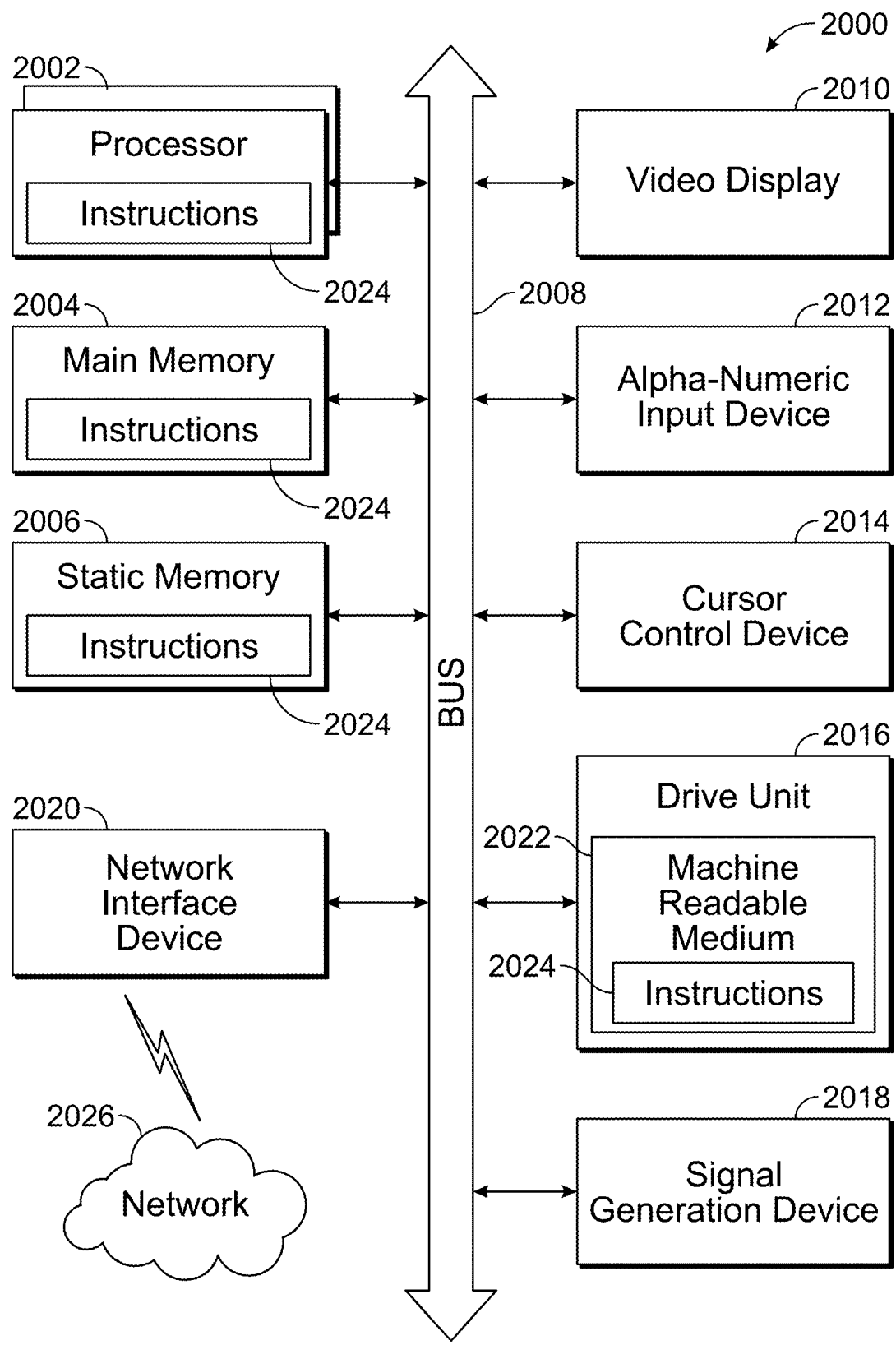
FIG. 9 shows a diagrammatic representation of a computing device for a machine in the example electronic form of a computer system, according to an example embodiment.

As mentioned above, the computer or processor 2000 and associated memory can be used to control many of the processes associated with analyzing the blood samples. FIG. 9 shows a diagrammatic representation of a computing device for a machine in the example electronic form of a computer system 2000, according to an example embodiment. In various example embodiments, the machine operates as a standalone device or can be connected (e.g., networked) to other machines. In a networked deployment, the machine can operate in the capacity of a server or a client machine in a server-client network environment, or as a peer machine in a peer-to-peer (or distributed) network environment. The machine can be a personal computer (PC), a tablet PC, a set-top box (STB), a Personal Digital Assistant (PDA), a cellular telephone, a portable music player (e.g., a portable hard drive audio device such as a Moving Picture Experts Group Audio Layer 3 (MP3) player, a web appliance, a network router, a switch, a bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 2000 includes a processor or multiple processors 2002 (e.g., a central processing unit (CPU), a graphics processing unit (GPU), arithmetic logic unit or all), and a main memory 2004 and a static memory 2006, which communicate with each other via a bus 2008. The computer system 2000 can further include a video display unit 2010 (e.g., a liquid crystal display (LCD) or a cathode ray tube (CRT)). The computer system 2000 also includes an alphanumeric input device 2012 (e.g., a keyboard), a cursor control device 2014 (e.g., a mouse), a disk drive unit 2016, a signal generation device 2018 (e.g., a speaker) and a network interface device 2020.

The disk drive unit 2016 includes a computer-readable medium 2022 on which is stored one or more sets of instructions and data structures (e.g., instructions 2024) embodying or utilized by any one or more of the methodologies or functions described herein. The instructions 2024 can also reside, completely or at least partially, within the main memory 2004 and/or within the processors 2002 during execution thereof by the computer system 2000. The main memory 2004 and the processors 2002 also constitute machine-readable media.

The instructions 2024 can further be transmitted or received over a network 2026 via the network interface device 2020 utilizing any one of a number of well-known transfer protocols (e.g., Hyper Text Transfer Protocol (HTTP), CAN, Serial, or Modbus).

While the computer-readable medium 2022 is shown in an example embodiment to be a single medium, the term "computer-readable medium" should be taken to include a single medium or multiple media (e.g., a centralized or distributed database, and/or associated caches and servers) that store the one or more sets of instructions and provide the instructions in a computer readable form. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, tangible forms and signals that can be read or sensed by a computer. Such media can also include, without limitation, hard disks, floppy disks, flash memory cards, digital video disks, random access memory (RAMs), read only memory (ROMs), and the like.

A computer that executes a set of instructions is transformed into a specialized machine having a specific functional purpose.

It should be noted that the examples set forth above all deal with the sampling and processing of dried blood to test for various and assorted diseases and other maladies. It should be understood that the testing system could be used to collect and analyze other fluids or other bodily fluids for collection of samples and analysis of the same.

The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

It should be noted that the sampling device 200 and a system that uses the sampling device 200 has many advantages over the DBS-cards. Among the advantages are that less blood is required for obtaining a sample or multiple samples. As a result, a smaller lancet that makes a smaller wound can be used. This translates to less pain for test subject or patient. The sample device can be handled by a robot. In one example, a robot can handle the sample via the handle and stem of the sample device. As a result, sample preparation can be more easily automated. The sample device or a system that uses a plurality of sample devices is also more amenable to complex sample preparation schemes, such as those that require multiple extraction solvents and/or multiple stages. In addition, when using the sampling device 200, the entire sample is used in the extraction. This avoids the problem of sampling a subset of heterogeneous blood spot contained on the DBS-card. Yet another advantage is that the sampling device 200 is far less prone to contamination during the sample collection, shipment and sample preparation procedures. Still another advantage is that the sampling device 200 allows for direct determination of the original blood sample volume which can then be used for subsequent analytical calculations.

Identity-Authentication, Timestamp, Environmental Conditions Tracking.

Various embodiments described herein relate to a blood sampling apparatus including an identity-authentication device and method to verify the individual who is providing the blood, a record of the sample collection time, blood sample characteristics, environmental conditions, sampling location and a device and method to determine hematocrit levels and the volume of blood loaded on the blood collection apparatus described herein.

Figure 10:
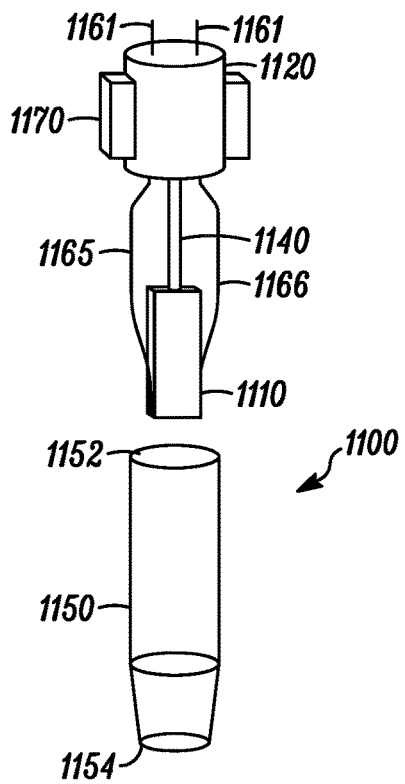
FIG. 10 is an exploded perspective of a sample collection system, according to an example embodiment.

FIG. 10 is an exploded perspective of a sample collection system 1100, according to an example embodiment. The sample collection system 1100 is a broad overview of device that has been previously reported in US patent application entitled "FLUID SAMPLING APPARATUS AND METHOD" (publication number 20140276217). The sample collection system 1100 includes a handle-stem-paper unit comprising the handle 1120 the stem 1140 and the absorbent paper 1110. The handle 1120 has been designed with features such as 1170 that makes the device amenable to robotic manipulation that is used to process the sample. The system also includes a protective cover 1150 which shields the absorbent material 1110 from the external environment. An important addition to this device are one or more electrodes shown here as two wires 1165 and 1166. These wires terminate the top of the apparatus 1161 and near the terminal end of absorbent material 1110 which is opposite the stem 1140.

Figure 11:
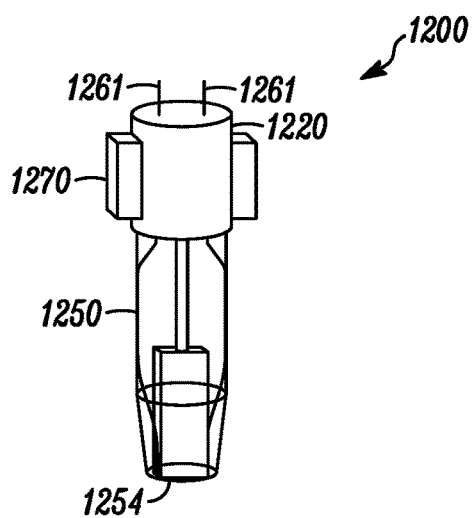
FIG. 11 is a perspective view of the sample collection system showing the protective cover positioned over the absorbent paper, according to an example embodiment.

FIG. 11 is a perspective view of the sample collection system showing the protective cover positioned over the absorbent paper. This is the arrangement of the apparatus used during the blood collection process and therefore the protective cover 1250 shields the absorbent material 1110 from contaminants originating from the external environment. Opening 1254 allows the transfer of the sample from the environment to the absorbent material and this opening is near the termination of wires 1165 and 1166 shown in FIG. 1.

Figure 12:
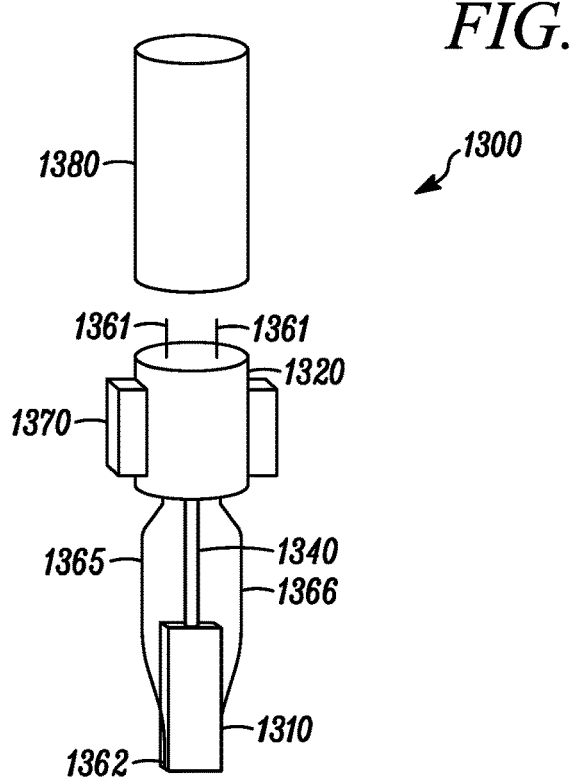
FIG. 12 is an exploded perspective view of the sample collection system showing the blood collection system without the protective cover, according to an example embodiment.

FIG. 12 is an exploded perspective view of the sample collection system showing the blood collection system without the protective cover 1250. Unit 1380 attaches to unit 1320 and is designed to be attached during the blood collection process and or during the transfer of the blood collection device 1300, including protective cover 1250, to a sample processing facility. Unit 1380 is a data logging system with sample and environmental sensors.

Unit 1380 makes physical contact and can be fastened to unit 1320. Unit 1380 might contain some or all of the features: a memory system, a computer processor, a real time clock, a GPS (global positioning system), environmental sensors that can track temperature, humidity, luminosity, and atmospheric pressure. Unit 1380 might also contain an accelerometer to track movement of the apparatus 1300 either by human or non-human manipulation. Unit 1380 makes physical contact to one or more wires or conductive materials depicted here as wires 1365 and 1366. These wires act as probes that can sense when blood has been loaded onto the absorbent material 1310. Unit 1380 might be physically connected or the same physical unit as unit 1320.

Figure 13:
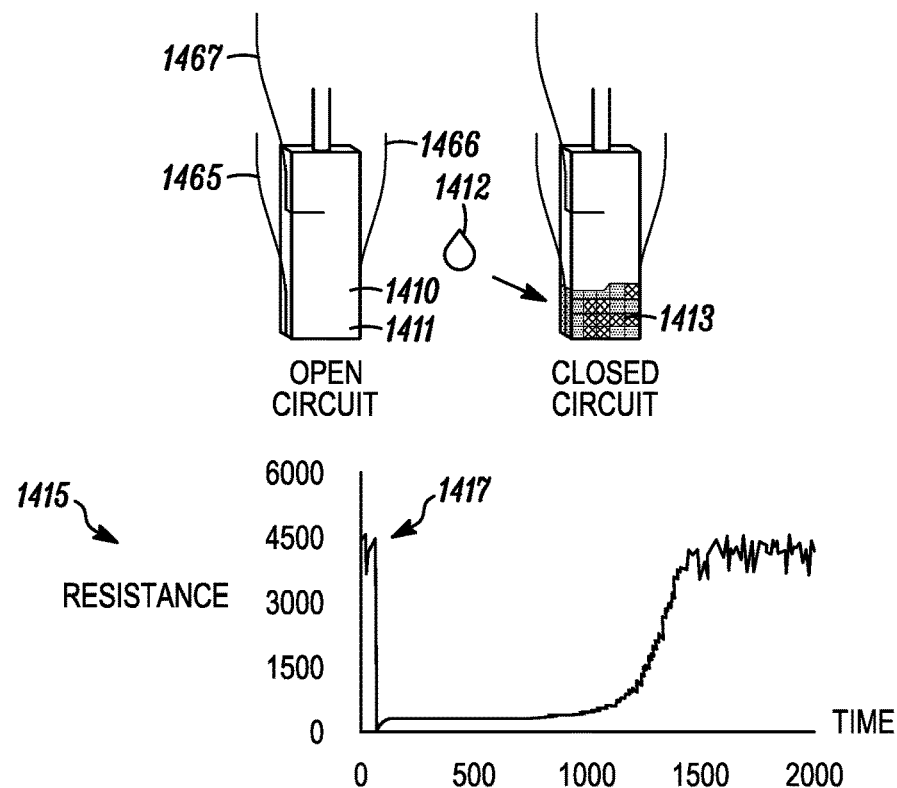
FIG. 13 is a zoomed in perspective view of the area of the absorbent paper proximate to opening 1254 depicted in FIG. 11, according to an example embodiment.

FIG. 13 is a zoomed in perspective view of the area of the absorbent paper proximate to opening 1254 depicted in Figure. 11. Wires 1465 and 1466 comprise an open circuit exists when the absorbent material is in a blood-free state 1411. When blood 1412 is deposited on the absorbent material, wires 1465 and 1466 make electrical contact and therefore closes the circuit as electrons are passed to or from wire 1465 through the blood wetted absorbent material 1413 to or from wire 1466. This circuit closing event is referred to here as the "blood-collection-trigger" and is triggered by the absorbent material starting at state 1411 and transitioning to state 1413. The inset graph 1415 shows a plot of the resistance as it varies with time, with the resistance relating to the conductive path between electrode 1365 and 1366 referred to here as the "absorbent-material-resistance" (see Experimental). The point in time 1417 indicates when blood was deposited onto absorbent material 1410. This plot shows that the signal to noise is sufficiently high to accurately detect the blood-collection-trigger as the absorbent-material-resistance in state 1411 is approximately three orders of magnitude higher, mega-ohms range, compared to state 1413 where the resistance is in the kilo-ohms range. This resistance based detector could be substituted by other detection methods that would track other commonly measured electrical properties.

Furthermore, the wires 1465 and 1466 can be probes to measure a variety of electrical properties including: electrical inductance, resistance, conductance, capacitance of the blood or blood-wetted-material. Some or all of these electrical properties can be monitored before, during and after the blood loading process thereby creating a means to determine the precise point in time when the blood was deposited onto the apparatus. An additional electrode could be place on the absorbent material 1410 in such a way to determine if the maximum amount of blood capacity, of the blood collection device, was reached. Furthermore, a plurality of electrodes could be positioned on the paper to determine where the blood had been positioned on the absorbent material 1410.

The electrodes shown here as 1465, 1466, 1467 and described above could be arranged on or in close proximity to the absorbent material. The electrodes could be made of wires derived from metals or other conductive materials. The electrodes could also be made of conductive paints applied directly to the absorbent material or other parts on the apparatus. The conductive paint could be graphite-based or metal-salts-based (e.g., silver nitrate) or liquid-metal-based (e.g., gallium indium alloy) or metal-nanoparticle-based. The liquid conductors could be applied to the absorbent material 1410 by ink jet printing methods. The electrode could be made of a combination of two or more conductive materials. In the same way, the conductive path from the electrode end on or near the absorbent material to point 1361 can be made of a combination of two or more conductive materials.

Figure 14:
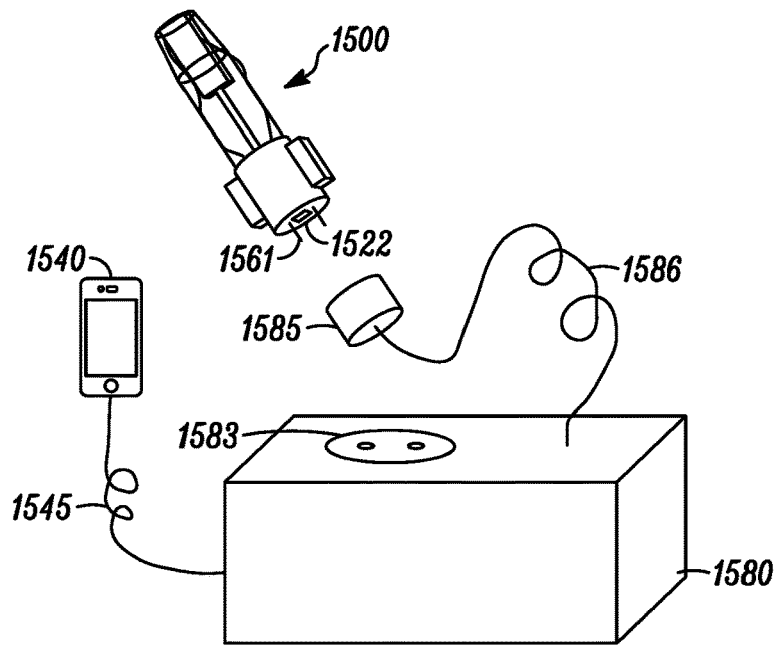
FIG. 14. is a perspective view of the sample collection system showing the blood collection system, according to an example embodiment.

FIG. 14. is a perspective view of the sample collection system showing the blood collection system 1500. Unit 1580 can have some or all of the same functionality as unit 1380 as described above. However 1580 is designed to be used during the the blood collection process and blood drying period and is not specifically designed for transportation but could be used during the transportation process. Unit 1580 could function as a blood drying station and, like unit 1380, can function as a data logging system with sample and environmental sensors as described above.

Unit 1580 makes physical contact to one or more wires or conductive materials depicted in FIG. 3 as wires 1365 and 1366. These wires act as probes that can sense when blood has been loaded onto the absorbent material 1310 as shown in FIG. 3. In one embodiment, physical contact of wires 1561, to electrical contacts located in base mount 1583, would occur when blood collection device 1500 is placed on mount 1583. In another embodiment, physical contact of wires 1561, to electrical contacts in remote connector 1585, would occur when blood collection device 1500 is fastened to remote connector 1585 and in this embodiment remote connector 1585 is connected to unit 1580 by connecting wire 1586. Remote connector 1585 could be connected to unit 1580 by a wireless connection. In all embodiments mentioned here, wires 1365 and 1366 can be connected to the electronics in unit 1580.

A unique identifier 1522 could be a barcode or a qr code or another identifier which could be recognized or scanned by unit 1580 by virtue of a camera or identifier or sensing device contained in unit 1583 or 1585. This scanner could be a RFID scanner or another wireless identification system. Furthermore, the identifier could be in the form of a digit object stored in a memory unit contained in unit 1500. This digital object or identification tag would be read by unit 1583 or 1585.

In another embodiment, unit 1581 might connect or mount onto the mobile device 1545 through a physical mount, or by using the usb port, charging port, headphone jack, other electrical ports or a wireless connection. In this embodiment, unit 1581 would be stationed directly onto the mobile device 1540.

Unit 1380 or 1580 might contain a USB port or other communication port that can transfer information or data from the internal memory or a serial data feed or similar to the memory or processor of mobile device 1540. The memory and or the processor in 1680 or 1681 could be supplied by the memory and processor of the mobile device 1640.

Items of units 1380 and 1580 might be mixed and or swapped between the two units thereby producing a hybrid unit that is not depicted here in figure-form.

Figure 15:
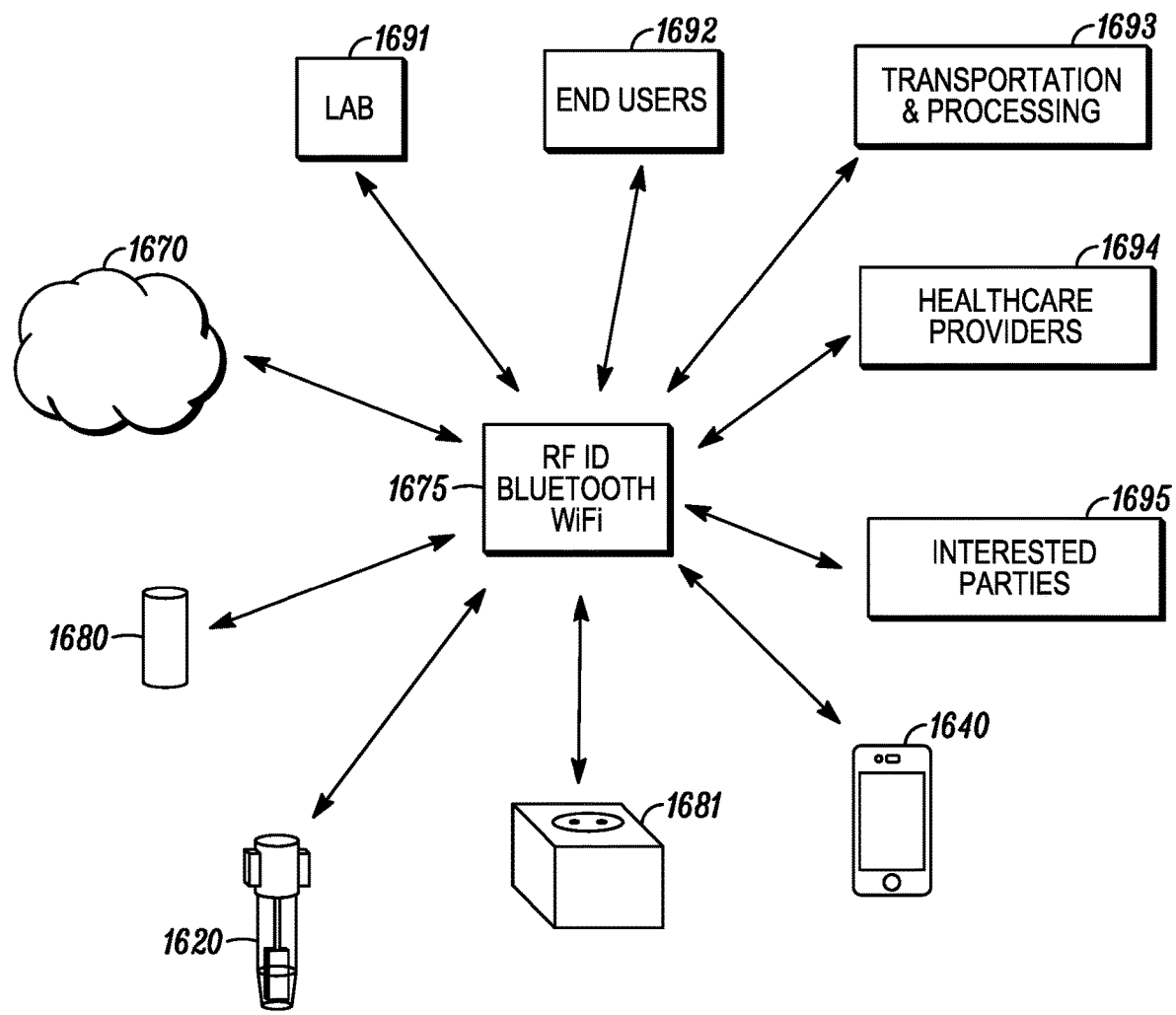
FIG. 15. is a schematic showing the network diagram of a system that allows the transfer of data to and from blood collection device units, to and from other devices, facilities, individuals and entities involved in the collection, transportation, processing, analysis and consumption of the blood sample and the related blood test, according to an example embodiment.

FIG. 15. is a schematic showing the network diagram of a system that allows the transfer of data to and from blood collection device units 1620, 1680, 1681 to and from other devices 1640, facilities 1691 and 1693, individuals such as the blood donor 1692 and entities 1649, 1695 involved in the collection, transportation, processing, analysis and consumption of the blood sample and the related blood test.

The process of shipping by postal service, private carrier such as FedEx for example, or by drone pickup is another means of transferring data from blood collection device units 1620, 1680, 1681 to other items shown in FIG. 15. Once units 1620, 1680, 1681 arrive at any authorized location shown in FIG. 15, the memory on units 1620, 1680, 1681 could be accessed by electrical or wireless connection to other memory or processors on the network 1675.

Referring back to FIG. 13, the "blood-collection-trigger" occurs when blood is deposited on the absorbent material 1410 the circuit is closed 1413. This closing of the circuit is an event that any processor-containing-item shown in FIG. 6 could detect.

The circuit closing event could trigger any processor shown in FIG. 6 to mark the event as the starting point of blood collection referred to here as the "sample-timestamp". Also the sample-timestamp is a point in time when the blood-wetted absorbent material 1410 begins to dry. The sample-timestamp can then be uploaded to other memory systems on the network 1675 to be processed by other processors on the network with the ultimate goal of recording the point in time that the blood sample was collected.

This blood-collection-trigger could initiate an email being sent to interested parties 1695 such as the individual who is undergoing the blood collection 1692, healthcare service providers 1694, laboratory personnel to name a few. The blood-collection-trigger could also initiate operations at an autonomous or semi autonomous sample processing facility or sample analysis laboratory 1693. Also, the blood-collection-trigger could initiate a pickup by a shipping service through ground or drone delivery vehicles that are manned or unmanned.

Furthermore, the blood-collection-trigger could activate an embedded transponder contained on, near or inside of blood collection device 1620 or 1680 or 1681 or other items described herein and this transponder could interact with unmanned or manned shipping assets 1693 to aid in the geolocation and or pick up of the blood sample for eventual delivery to a processing facility 1693 or laboratory 1691 for analysis.

Additional information about the blood sample, the environment and the user can be collected and or transferred to other processors and memory systems on the network 1675. This data can then be used to aid in the processing and analysis of the collected blood. This data can include electrical inductance, resistance, capacitance, conductance, environmental temperature, environmental humidity, atmospheric pressure, accelerometer data and geolocation contained on unit 1680 or 1681 or 1640.

Figure 16:
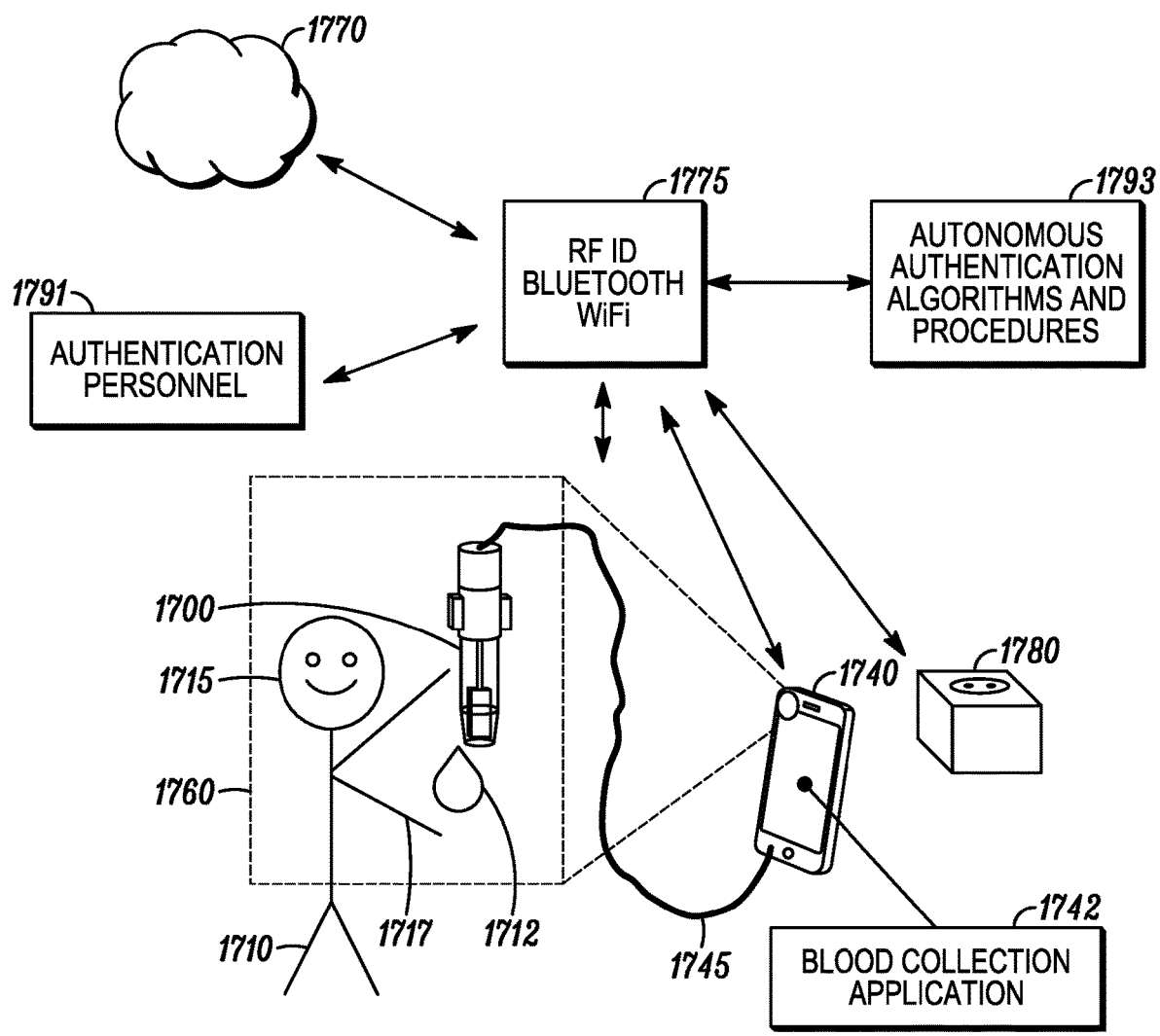
FIG. 16 is a schematic that shows a procedure to verify the identity of an individual who is providing the blood during a blood collection procedure in which only the blood provider is required to be present, according to an example embodiment.

FIG. 16 is a schematic that shows a procedure to verify the identity of an individual who is providing the blood during a blood collection procedure in which only the blood provider is required to be present. The publication entitled "Patient Portal Identity Proofing and Authentication Guidance from the HIMSS Identity Management Task Force, 2016" outlines typical ways organizations perform two types of procedures related to verifying the identity of an individual. The first type of procedure is to prove the identity of an individual and enter them into the organization's computer system and this is called "identity-proofing". The second type of procedures are routine authentication protocols to verify the identity of an individual in order to provide a patient, for example, access to online portals to health-records and this is called "identity-authentication". The scheme shown in FIG. 7 and described herein is primarily designed to function as an identity-authentication procedure, however all aspects of this procedure could be applied to "identity-proofing".

Referring back to FIG. 16, the provider of the blood 1710 is holding a blood collection device 1700 that is connected to a mobile device 1740 or station 1780 or secure network 1775. The data connection from the blood collection device 1700 to mobile device 1740 or station 1780 might be through the physical electric connection 1745 or the secure network 1775. The mobile device 1740 has a camera that is capturing an image or movie with an outline 1760 and this camera could be the forward facing or rear facing camera of the mobile device 1740. The image or movie frame 1760 contains the face 1715 and the blood-producing finger 1717 of the individual 1710 and the blood collection device 1700. Also, the image 1760 or each movie frame 1760 could have a timestamp associated to the point in time the image or frame was captured and this is referred to here as the "image-timestamp". Station 1780 could have a camera and other features that are common on a mobile device and therefore the mobile device 1740 could be replaced by unit 1780 without losing any capabilities described here with regards to the authentication procedure.

In one embodiment, station 1780 could be designed to support or hold the mobile device 1740 so that the camera on the phone captures the items listed above. Or a separate unit could function as this support. This physical support could allow for the screen of the phone to face the blood donor, therefore the mobile application 1742, used during the blood collection procedure, could be used to direct messages and instructions to the blood donor.

The following list, the "Blood-donor-identification-authentication-protocol" contains some or all of the elements that could be used in the blood collection procedure and would result in verification of the identity of the blood donor 1710. The items listed here could be rearranged, substituted, eliminated, expanded on and in doing so the identification-authentication protocol could be tailored to a specific application. The list below represents a general example of an identity-authentication protocol that could be used.

Blood-donor-identification-authentication-protocol:
16.1. The user logins or unlocks their mobile device with procedures typical to mobile device operating systems.
16.2. The user opens a blood collection mobile application 1742 and logins in via any of the methods: username/password combo, fingerprint sensor, retina scan, facial recognition, voice authentication, RSA key fob, SMS message containing an access code, one factor authentication, two factor authentication.

16.3. The user connects all devices together which could include items 1700, 1740, 1745, 1780.

16.4. Blood collection device 1700 is connected to the authentication station which could be the mobile device 1740 or station 1780 or another connected device such as a laptop computer.

16.5. The blood collection device 1700 could be scanned at this point to confirm the identity of the device.

16.6. The authentication station could be place in a way to capture images or movies of the blood collection procedure.

16.7. Movie recording could begin.

16.8. The blood donor 1710 could begin the blood collection procedure while remaining in the movie frame. These steps include antiseptic wipe and lancet finger puncture to produce a blood drop on the finger 1712.

16.9. The blood collection device 1700 could then be place near the blood drop 1712.

16.10. The blood is transferred to the blood collection device 1712 and the "blood-collection-trigger" occurs.

16.11. The blood-collection-trigger could initiate image capture of items in 1760, authentication procedures including a fingerprint scan, retina scan, facial recognition, voice authentication, activation of authentication processes 1793 on other processors on network 1770 and activation of other employees or entities 1791.

16.12. A question could be submitted to the user blood donor 1710 via a phone call, an application 1742 based prompt, an email question or sms question. Upon a valid answer to the question the confidence of the identity is increased.

Any authentication algorithm described herein could be performed on a processor-containing item shown in this application or connected to network 1775. This authentication algorithm could compare the sample-timestamp with the image-timestamp that is associated with the image 1760 that shows when the initiation of the blood collection event or the moment in time when absorbent material goes from state 1411 to state 1413. If these two timestamps, the sample-timestamp and the image-timestamp do not agree to within a few milliseconds or a few seconds or a few minutes, for example, the identification could be invalidated.

It might be the case that images of individuals might not be permitted to be transferred to secure networks due to regulatory limitations. In this case some or all of the facial regulation process or algorithm could be performed on the remote processor which can access the image of the individual. In this way, the limitation of not being allowed to transfer the image of the individual to the secure network, is resolved.

The schemes and elements shown in FIG. 13, 14,15, 16 and described elsewhere provide the means to have a "formless" or "paperless" blood collection process where the blood donor 1710 does not have to write down or enter on paper the point in time (sample date and sample time) when the blood sample was collected. This is the case as the sample-timestamp replaces the need to physically log the point in time when the blood was collected via paper-based forms or by paper-less forms such as physical entry into a computer system through keyboard entry or voice entry.

Furthermore the scheme outlined in FIG. 16 describes how the identity of the blood donor can be verified, thereby associating the blood collection device 1700 to this authenticated individual. In healthcare organizations, this is typically accomplished by associating pertinent items such as a blood sample, for example, which has a unique code to an individual's MRN or "medical record number". The blood collection device 1700 would have a unique code that could be associated with a unique code of the identity-verified or identity-authenticated blood donor such as a MRN. This process would eliminate the need for the blood donor 1710 to physically enter their name, sample date and sample time into a paper or paperless form.

Alternatively, in cases where there is not a requirement to authenticate the identity of the blood donor, the association of the unique identifier of the blood collection device 1700 or 620 to the unique code associated with the blood donor could be accomplished by steps outlined in the blood-donor-identification-protocol list excluding or not requiring some or all of the steps 16.1, 16.2, 16.6, 16.7, 16.8, 16.11, 16.12. This is a less rigorous protocol that would associate the blood collection device that will be used or was just used to collect the blood sample to the blood donor and the point in time when the sample was collected. This is another method that eliminates the need for the blood donor 1710 to physically enter their name, sample data and sample time into or onto a paper or paperless form.

Figure 17:
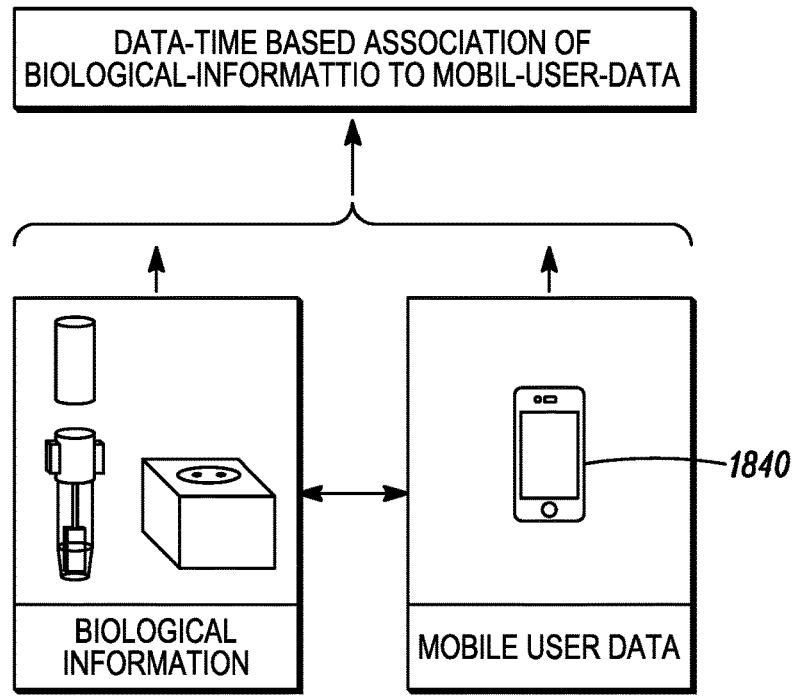
FIG. 17 describes how biological information can be associated with mobile-user-data, according to an example embodiment.

FIG. 17 describes how biological information can be associated with mobile-user-data. Data related to the owner of the mobile device 840 could be uploaded from the mobile device to other systems on the network. This data could include fitness data such as step counter or other accelerometer data related to the movement or activity level of the owner, heart rate, body temperature, diet information from mobile apps, medical information including health information, stress information and drug usage history from mobile apps or EMR systems or EMR portals or other health and wellness mobile apps, email content, text message content, geolocation history, consumer purchase data from mobile apps, text and voice string search and submitted to mobile apps or mobile operating systems. All this data will be referred to here as "mobile-user-data".

The blood-collection-trigger could 1) initiate upload of mobile-user-data and or 2) initiate a database connection of the mobile-user-data contained on the mobile device 640 to the blood sample and ultimately, after blood analysis, to the chemical, genetic and physical properties of the blood (biological information). Connecting the blood properties to mobile-user-data is a method to connect biological information of the user or health outcomes with lifestyle data or health inputs thereby allowing for the discovery of unknown correlations of health inputs to health outcomes.

Furthermore, the identity-authentication procedure described above could be used to provide access to EMR portals and therefore all data mentioned here and or contained on EMR systems could be uploaded or downloaded to and from an EMR access point or other secured access portal of another entity or organization containing data.

Method to Determine the Volume of Blood Loaded Onto the Apparatus.

Determining the amount of blood loaded onto absorbent material 1110 is required for the processing of the blood collection device 1100 described herein. A previous publication entitled "FLUID SAMPLING APPARATUS AND METHOD" (publication number 20140276217) describes one approach to determine the amount of blood loaded onto absorbent material 1110. In this previously reported invention disclosure, the volume of the blood loading is determined by analysis of a digital image of the blood wetted absorbent material 1110. Described herein is a novel method to determine the amount of blood loaded onto absorbent material 1410 and this method utilizes electrodes 1165 and 1166 which are described above.

Figure 18:
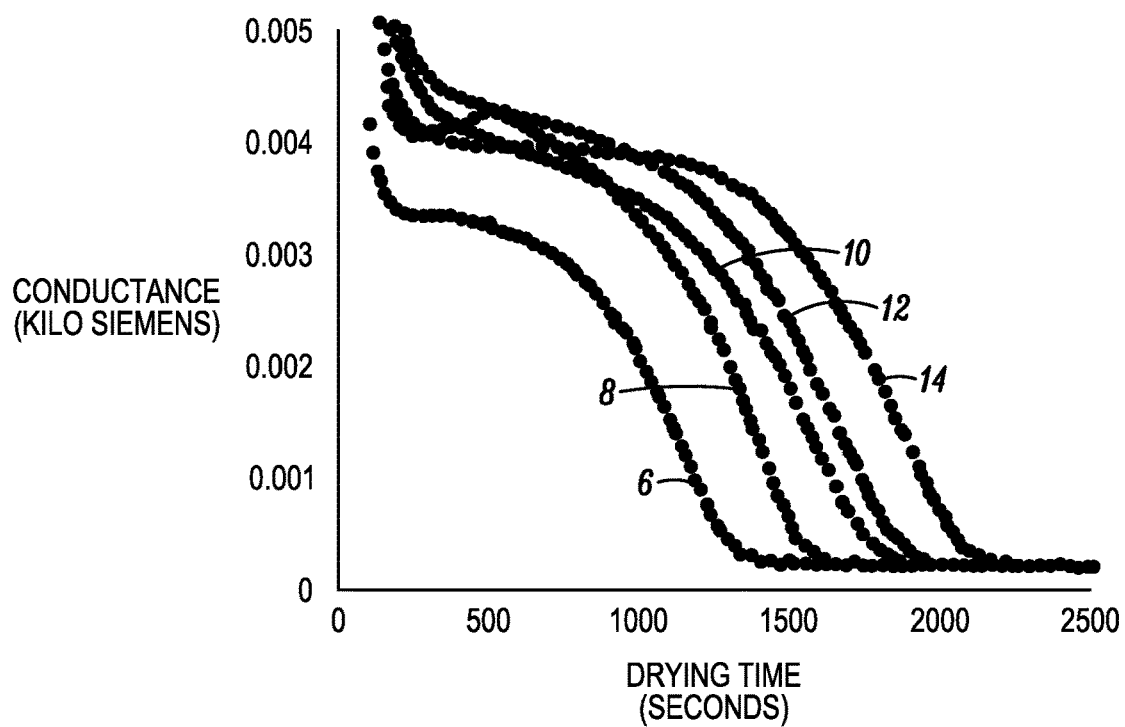
FIG. 18 is a plot of how the conductance or the inverse of the resistance of the blood wetted material 1413 changes from the blood-collection-trigger or time zero seconds to 2,500 seconds, according to an example embodiment.

FIG. 18 is a plot of how the conductance or the inverse of the resistance of the blood wetted material 1413 changes from the blood-collection-trigger or time zero seconds to 2,500 seconds (see Experimental for details). There are five individual curves each corresponding to absorbent material 1410 loaded with a different amount of blood: 6, 8, 10, 14, 16 μL and these volumes are labelled for each curve. All five curves in FIG. 9. were produced from blood with a hematocrit level of 50. FIG. 9 shows that the time required to reach a minimum conductance increases as more blood is deposited onto absorbent material 1410. Presumably the conductance decreases due to water loss from evaporation. The loss of water, which is the aqueous solvent system in blood, results in a decreasing abundance or concentration of charge carriers (ionic molecules) remaining in the aqueous solution. This decrease abundance of solubilized charge carriers correlates to a decrease in the conductance of the blood wetted absorbent material.

Figure 19:
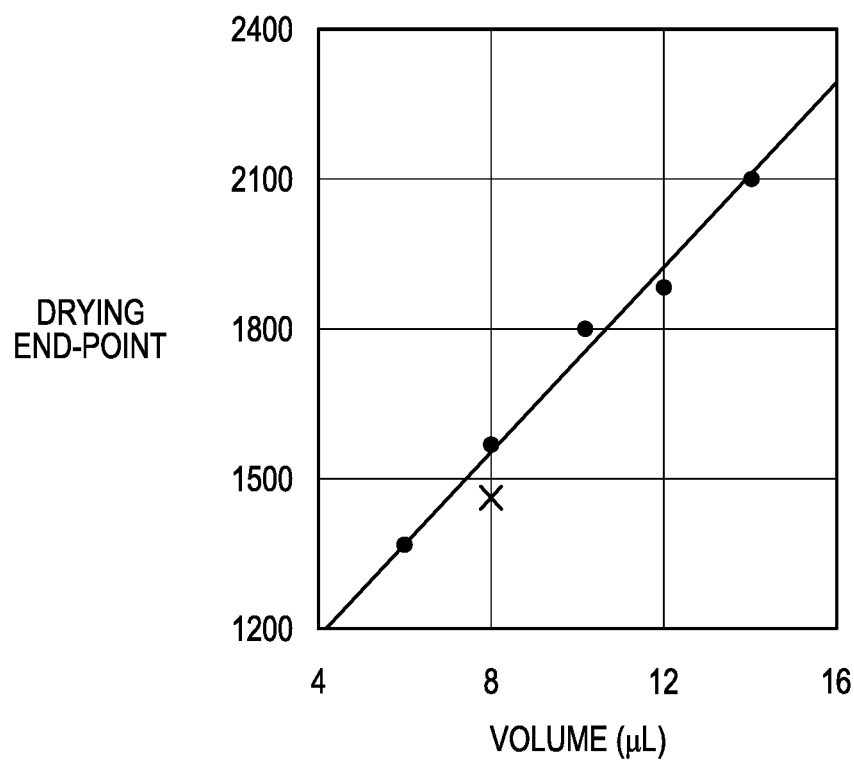
FIG. 19 Is a plot that shows a linear relationship between the "drying-end-point" and the amount of blood loaded onto absorbent material, according to an example embodiment.

FIG. 19 Is a plot that shows a linear relationship between the "drying-end-point" and the amount of blood loaded onto absorbent material 1410, these data points are displayed as solid circles (see Experimental for details). The drying-end-point is produced from the conductance drying curves (FIG. 18.) by determining the peak center of the plot produced by taking the second derivative of the conductance drying curve (see FIG. 26).

This linear relationship shown in FIG. 10 can be a basis for calculating the amount of blood loaded onto a blood collection device 1100 in cases where the amount of blood loaded is unknown. This situation could occur when blood collection device 1100 is used in uncontrolled or remote environments and carried out by untrained individuals. This situation could be home-blood collection for example, with units 1380 or 1580 performing the conductance drying curve measurements.

Furthermore, this conductance based determination of blood volume is independent of the hematocrit level and this is an important feature as dried blood spot sampling has been plagued with the "hematocrit problem" which is described above. In FIG. 10, at 8 μL volume, there are three data points represented by an "x" mark (these three points overlap) and these points correspond to 8 μL loading volume at blood hematocrit values of 24, 50 and 76. The tight grouping of the points at a variety of hematocrit levels shows that the drying-end-point is highly independent of the hematocrit level and depends primarily on the volume of blood loaded onto absorbent material 1110 (see FIG. 27).

Shown in the list called "Conductance determination of blood volume protocol" is an example protocol for using the relationship shown in FIG. 10 to determine an unknown blood loading volume onto absorbent material 1110.

Conductance determination of blood volume protocol:
Make a mathematical model where volume is a function of the conductance.
19.1.1. Make conductance-drying-curve plots as shown in FIG. 18. The plots could be made with a variety of blood loading volumes and drying times. Furthermore, the humidity and temperature and atmospheric pressure affect the drying dynamics and therefore the conductance-drying-curve plots. Given this, it would be useful to make a series of conductance-drying-plots carried out at combinations of humidity, temperature and atmospheric pressure. The combinations of temperature, humidity and atmospheric pressure could be chosen to reflect conditions that would be experience in all imaginable and typical uncontrolled environments in which the blood collection device 1100 would be used.

19.1.2. For each conductance-drying-plot that is produced as described in 10.1, a corresponding drying-end-point vs loading-volume plots could be produced. A mathematical equation could be fit to the data in these plots. The mathematical equation or representation of this data could be a linear equation. This mathematical equation could then be used to calculate the volume of blood loaded on blood collection device 1100 when conductance-drying-curves are collected. An alternative method could utilize one multidimensional mathematical equation to describe all data points produced in 10.1.1. With this method the mathematical equation would have volume as a function of the conductance curve, temperature, humidity and atmospheric pressure.

Use the mathematical model to process samples:
19.2.1. In real world situations when the blood collection device 1100 is used to collect blood, the device 1300 or apparatus shown in FIG. 5 will be used to collect the temperature, humidity, atmospheric pressure and the conductance-drying-curve.

19.2.2. All the data described in 10.2.1 will be loaded into a memory device and or processor device that is contained on a piece of hardware that is connected to network 1675. Ultimately a processor will then calculate the drying-end-point for the blood collection device.

19.2.3. Next, a processor will use a predetermined mathematical equation (10.1.2) that mathematically relates drying-end-point to volume of blood loaded onto absorbent material 1110. The environmental conditions such as, temperature, humidity and atmospheric pressure, that were collected during the blood sampling (10.2.1) would be used to pick the most appropriate or best representative mathematical equation described in (10.1.2).

19.2.4. Finally the equation that was determined in 10.2.3 would be used to calculate the volume of blood loaded onto absorbent material 1110 from the drying-end-point that was calculated in 10.2.2. Alternatively, a multidimensional mathematical equation (described above) could use the conductance curve, temperature, humidity and atmospheric pressure to calculate the volume.

Method to Determine the Blood Hematocrit Level as a Means to Correct for the "Hematocrit Problem"

The "hematocrit problem" was introduced in the background section of this disclosure and describes the limitations of all dried-blood-spot based blood collection devices. The nature of the hematocrit-problem as it applies to dried-blood-spot blood collection is that for a given volume of blood loaded, blood with higher hematocrit levels take up less surface area of the absorbent material 1100 when compared to blood with lower hematocrit levels.

The previously disclosed method: "FLUID SAMPLING APPARATUS AND METHOD" (publication number 20140276217) can be improved by determining, estimating or approximating the blood hematocrit or blood viscosity. Furthermore, all conventional dried-blood-spot based blood collection devices can produce superior results if the blood hematocrit or blood viscosity can be calculated. Therefore this improvement could be applied to all dried-blood-spot based blood collection devices.

The original invention (publication number 20140276217) describes a process that takes a picture of absorbent material 1110 and uses that picture to determine the amount or volume of blood loaded onto that absorbent material 1110. Knowledge of this blood volume is used in subsequent processing of the sample. The invention described herein improves this previously described method by including a "hematocrit correction" to the original method. This improved method involves using an image of the blood spot to approximate the hematocrit level. In order to provide clarity for the subject matter, some of the previously invented items are described here.

Figure 20:
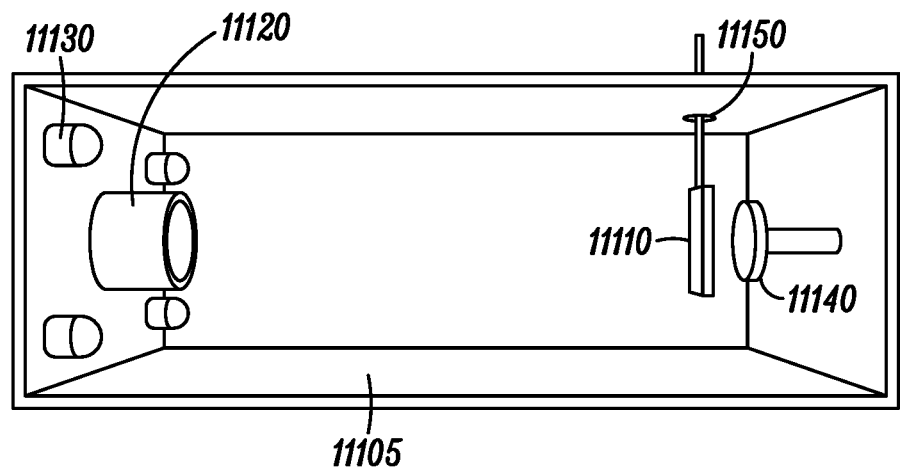
FIG. 20 Is a cutaway perspective view of a "photo-booth" where images of the absorbent material, which is part of a blood collection device, are captured, according to an example embodiment.

FIG. 20 Is a cutaway perspective view of a "photo-booth" 11105 where images of the absorbent material 11110, which is part of a blood collection device 1100, are captured. These images are produced by camera 11120. Illumination of the absorbent material 11110 results from one or a multitude of light sources 11130. The photo-booth has enclosed walls on all sides and this prevents illumination from external light sources. The blood collection device port 11150 allows for the absorbent material to enter the photo-booth 11105 however the dimensions of the port are sufficiently similar in size to the dimensions of the absorbent material to allow for a tight fit between the port and the absorbent material. Furthermore the lengthwise port pathway dimension is sufficiently long and this property together with the tight fitting nature significantly prevents light from entering the photo-booth and this is an important feature as it is ideal to control the source of light used to illuminate the absorbent material 11110.

The light source 11130 could be comprised of one or more than one individual light sources and these would be arranged symmetrically around or in relation to the camera 11120. The light sources could be of the type: incandescent, fluorescent, light-emitting-diode, to name a few. Additionally the light source could emit light at a specific electromagnetic wavelength or wavelength range. Furthermore two or more types of lights could be integrated into photo-booth 11105. For example, in one embodiment there could be four "white light" LEDs (light emitting diodes) and four IR LEDs (infrared or near-infrared LEDs) and this would allow the camera to capture two types of images: 1) a visible light image and 2) and infrared image. Capturing two types of images, a visible and infrared image, could be accomplished by capturing an image with one light source, on such as the visible light source, then the infrared light source could be switched on, while the visible light source is turned off and finally the second, infrared image could be captured.

The photo-booth 11105 also could contain one or a multitude of "image-standards" 11140 which are unchanging objects that appear in all images taken in the photo-booth 11105. The utility of these objects is to provide a means to have an unchanging object that has the properties of size and or color which can be compared across a multitude of images corresponding to a multitude of individual blood collection devices that might be loaded with a unique blood source of unique blood volumes.

Figure 21:
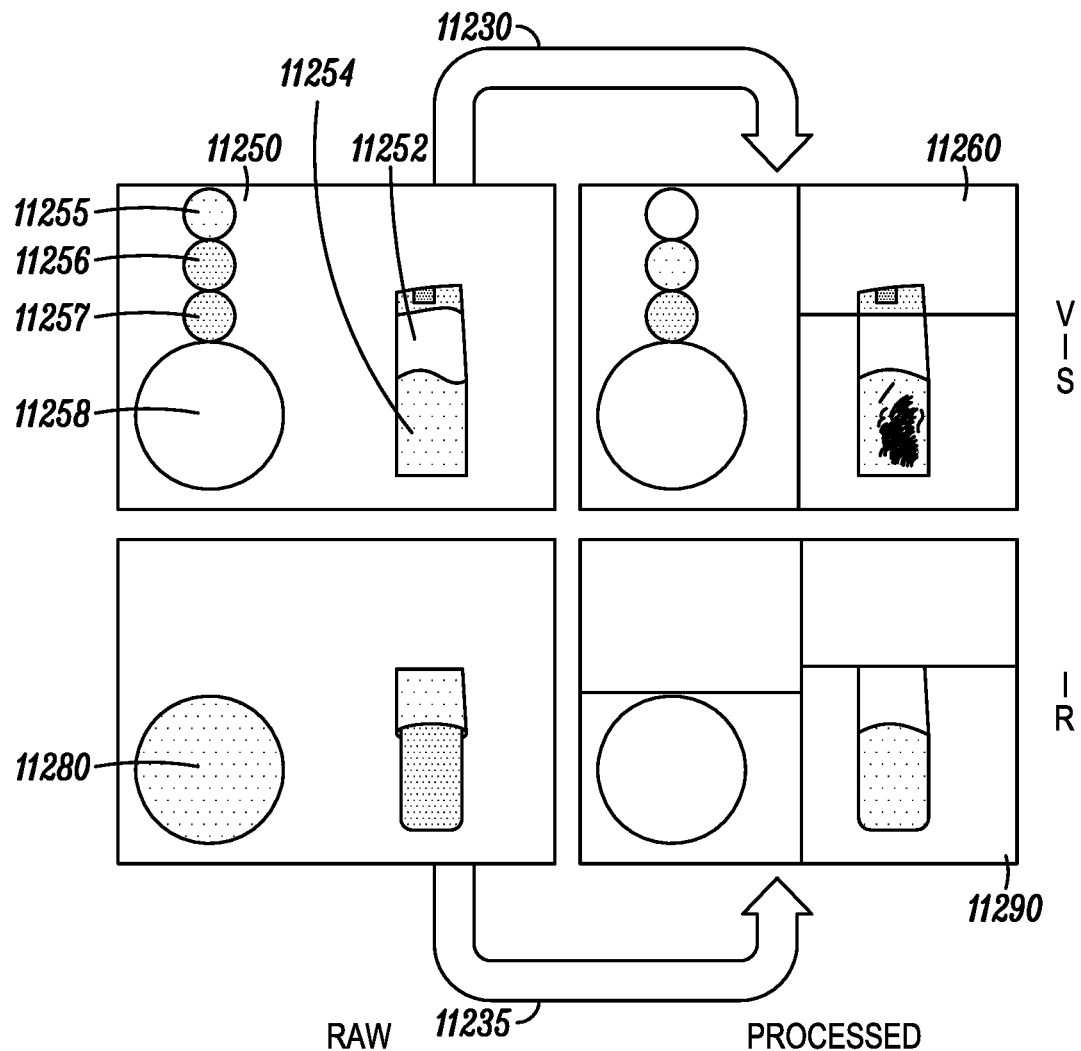
FIG. 21 is a collection of four images that were produced to analyze a single blood collection device, according to an example embodiment.

FIG. 21 is a collection of four images (11250,11260, 11280,11290) that were produced to analyze a single blood collection device 1100 (see Experimental for details). Image 11250 is a raw image produced by a camera situated in a similar manner to camera 1120. Image 11250 was produced by illuminating the absorbent material 1110 with white-light LEDs thereby producing a visual light image. In image 11250, the absorbent material 1110 has two distinct regions 11252 and 11254. Region 11252 is absorbent material 1110 which has not been wetted with blood. Region 11254 is is absorbent material 1110 which has been wetted with blood and then the blood has dried. Image objects 11255, 11256, 11257, 11258 are color or area standards. Object 11258 is a circle with a known area and therefore we refer to this object as an "area-standard". Objects 11255, 11256, 11257 are green, red, blue color standards and are used to control or understand how the color detected by the camera varies from one image to the next. In a similar manner, the absolute size of objects in the image can be calculated by comparing the object to the area standard.

Image 11260 is a processed or computer program generated image that is derived from the raw image 11250. The computer program 11230 analyzes each pixel of raw image 11250 and decides if the pixel represents the 1) black background, 2) one of four potential object-standards 11255, 11256, 11257, 11258) an unwetted and white region 11252 of absorbent material 1110 or 4) the blood wetted region 11254 of absorbent material 1110. The four regions are colored in the processed image 11260 according to the table below:

| REGION | REGION NAME | PROCESSED COLOR SCHEME |
| --- | --- | --- |
| r1 | "black-background" | Black |
| r2 | "image-standard-green" - 11255<br>"Image-standard-red" - 11256<br>"Image-standard-blue" - 11257<br>"Image-standard-area" - 11258 | 11255 = green, 11256 = red, 11257 = blue, 11258 = white |
| r3 | "white-region" - 11252 | white |
| r4 | "blood-region" - 11254 | Color gradient: red→yellow→green→blue. Red represents regions where the sum of the red, green, blue channels of the camera are the lowest and blue represents the highest red, green, blue channel sums. |

An important feature of the program 11230 is to count the number of pixels that correspond to regions r1, r2, r3, r4. Since the absolute area, in mm$^2$, is known for object-standard 11258 it is possible to convert the pixel count of the blood wetted region into an absolute area with the following formula:

$$\text{Area blood} = \text{area\_standard } 1258 * (\text{pixel\_count\_blood\_1254}/\text{pixel\_count\_standard\_1258})$$

By virtue of this process and the above calculation, this area value, in mm$^2$, corresponds to the blood wetted region 11254 and is comparable across a multitude of images that corresponds to a multitude of blood collection devices 1100.

One final feature of program 11230 is that the program keeps track of what region (r1,r2,r3,r4) each pixel corresponds to and this is stored into a memory system contained on, or connected to, a processing computer.

Image 11280 is a raw image produced by a camera situated in a similar manner as camera 1120 and is similar to image 11250. Image 11280 was produced by illuminating the absorbent material 1110 with IR LEDs (infrared LEDs) thereby producing an infrared light image. The regions are very similar to the regions described for image 11250. However the color standards 11255, 11256 and 11257 do not appear in image 11280 as the objects do not reflect or absorb enough of the IR radiation to be visible. The image 11280 appears to have a green tint and is darker than 11250. The camera and illumination settings used to produce image 11280 were optimized with the goal to produce a linear relationship between the hematocrit level of the loaded blood and the green channel of image 11280 and this relationship is shown in FIG. 13.

Figure 22:
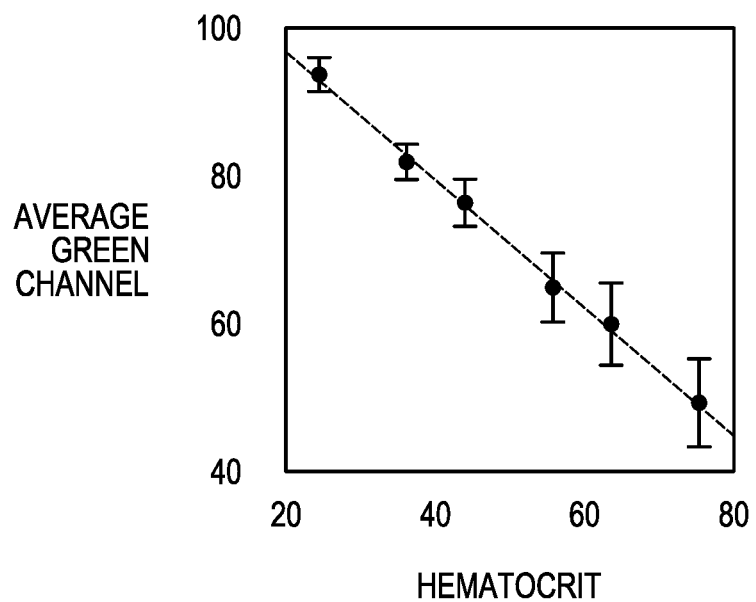
FIG. 22 shows the linear relationship between the blood hematocrit level and the the average green channel, of the blood-region, for a series of images that result from taking pictures of a multitude of blood collection devices loaded at a variety of hematocrit levels and blood volumes, according to an example embodiment.

FIG. 22 shows the linear relationship between the blood hematocrit level and the average green channel, of the blood-region, for a series of images 11280 that result from taking pictures of a multitude of blood collection devices loaded at a variety of hematocrit levels and blood volumes (see Experimental for details). The camera that captured the images that were used to produced FIG. 13, outputs images in the PNG (portable network graphics) format and this format has a red, green and a blue channel or value for each pixel. Program 11235 used the region information (r1,r2,r3, r4), that was stored in memory and was produced from image 11250 by program 11230. This region information is used to determine what pixels correspond to what regions (r1,r2,r3,r4). This results in the pixels of image 11280 corresponding to the the exact sample region (rl,r2,r3,r4) as that of image 11260. This method of pixel classification was used for the IR image 11280 as it was difficult to de novo classify the pixels solely from image image 11280. So image 11250 is used to classify the pixels of image 11280 and this works as all objects in both pictures are unmoved between the two pictures. This method also allows the program 11235 to accurately calculate the average green channel intensity for all pixels that correspond to the blood wetted region in the IR image 11280.

This relationship of the hematocrit to the IR-average-green-channel of blood-region can be the basis of a correction to the previously mentioned "hematocrit problem". The protocol to apply a "hematocrit correction" to analysis of blood collection device 1100 follows:

Hematocrit based blood volume determination protocol:
Make a mathematical model where volume is a function of area and IR data
22.1.1. Prepare or collect blood loaded blood collection devices at a variety of blood loading volumes and hematocrit levels.
22.1.2. Produce visible light images 11250 and IR light images 11280 as described above. Process raw image 11250 with program 11230 to produce processed image 11280 and similarly process image 11280 with program 11235 to produce processed image 11290. This step produces an area value (mm$^2$) and an IR-average-green-channel value that corresponds to the blood-region for each blood collection device.
22.1.3. Produce a 3-dimensional plot of volume-blood, area-blood-region and IR-average-green-blood-region (FIG. 28)
22.1.4. Fit the data in plot FIG. 28 (13.1.3) to a mathematical equation that accurately describes or models the data. Record the fitting parameters into a memory system on a processor.
Use the mathematical model to process samples:
22.2.1. For every blood collection device 1100 with an unknown amount of blood loaded onto the absorbent material 1110, produce and process the raw images 11250, 11280 and the processed images 11260, 11290 as described above. The output of this processing produces an area-blood-region value and an IR-average-green-blood-region value.
22.2.2. These two values can be entered into the mathematical model described above with the fitting parameters stored into memory and thereby a blood volume value is produced to be used for subsequent blood sample processing.

Figure 23:
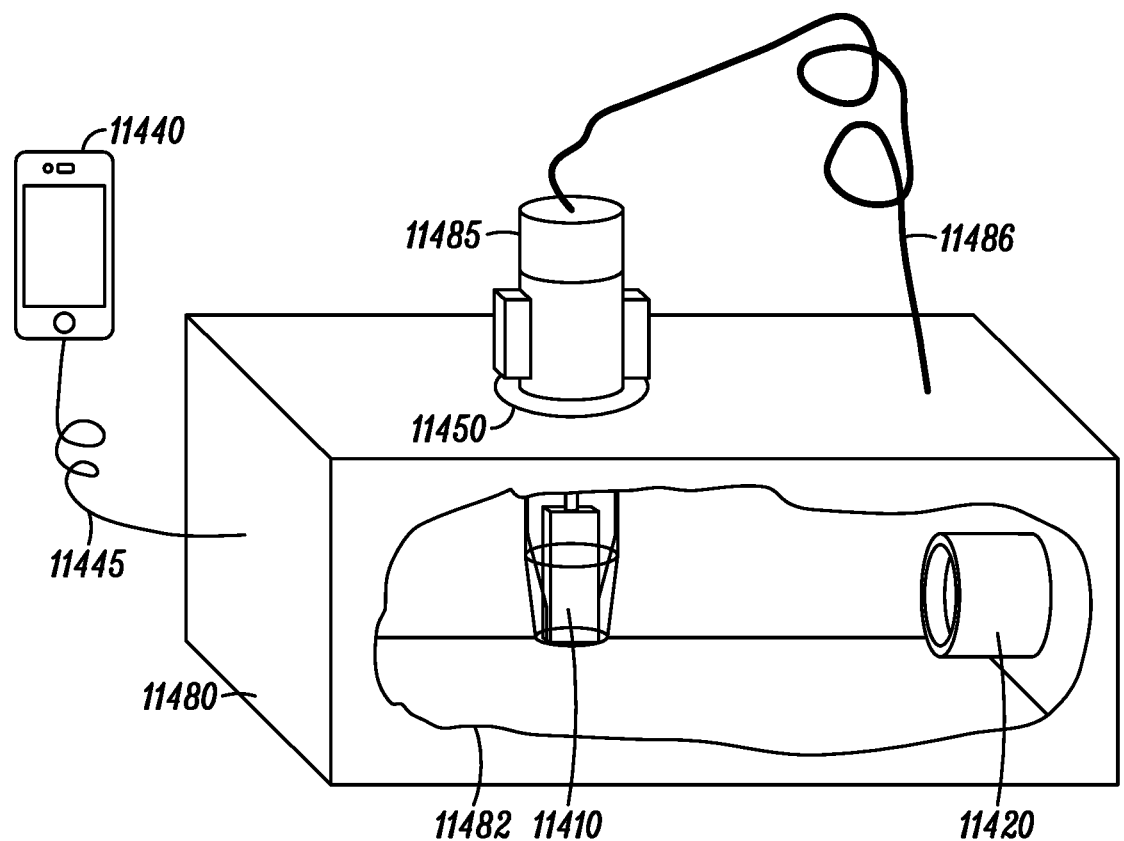
FIG. 23. shows a cutaway perspective view of unit 11480 which is a modified version of unit, according to an example embodiment.

FIG. 23. shows a cutaway perspective view of unit 11480 which is a modified version of unit 1580 (FIG. 5.). The cutaway region on the side wall is indicated by 11482. A camera 11420 is contained inside unit 11480 and this camera can perform the IR based blood volume determination with hematocrit correction described above. In addition, this remote station could perform all measurements and other functions as mentioned above for units 1580 and 1380.

Experimental

Figure 24:
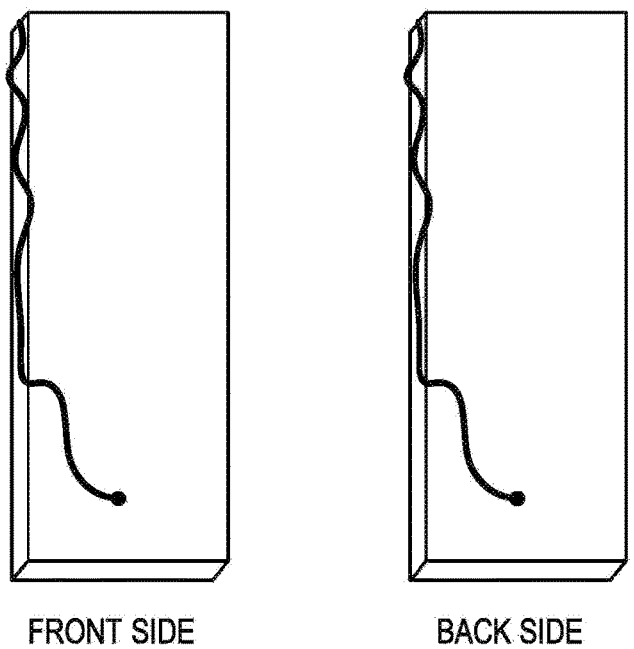
FIG. 24 shows an Arduino Uno micro controller configured to measure resistance of the absorbance material, according to an example embodiment.
Figure 25:
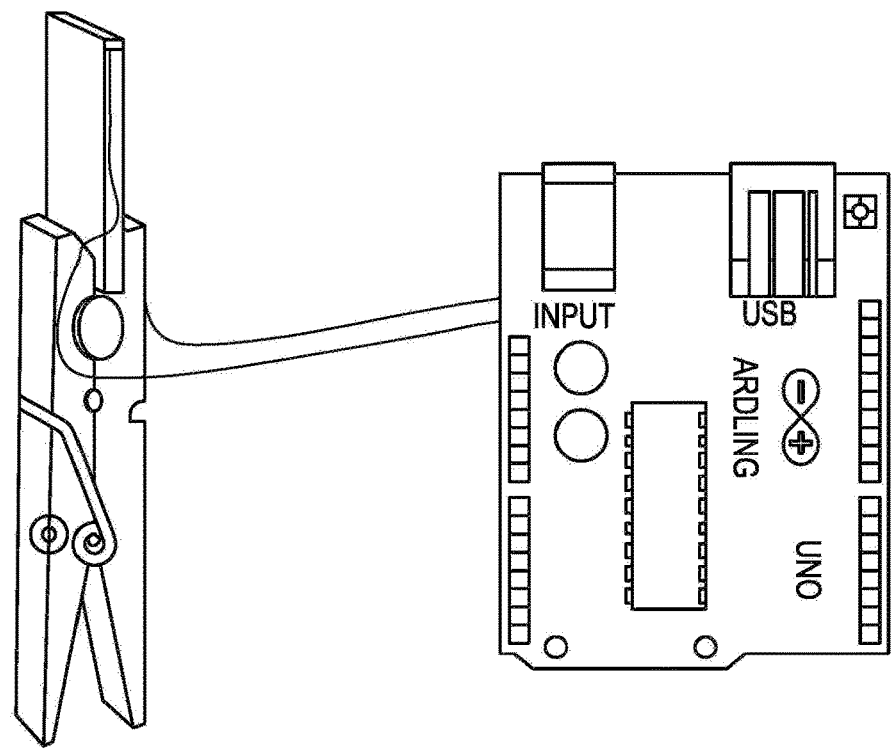
FIG. 25 is a set up showing a clamp contained two wire leads that made contact with both electrodes on the absorbent material, according to an example embodiment.

Blood Collection Device Electrical Experiments
Experimental Setup Used to Generate Conductance Drying Curves FIG. 24. An Arduino Uno micro controller was configured to measure resistance of the absorbance material 1110 (FIG. 25). Conductive Graphite Paint (Bare Conductive Electric Paint Pen, Bare Conductive London, 24 6LZ) was used to make electrodes on the absorbent material 1110 and this is shown below in FIG. E1 as the blue "painted" line. The absorbent material was 903 Paper (PN 10535097 Whatman qualitative filter paper Grade CF 12 sheets, W×L 210 mm×297 mm) was cut into rectangle with dimensions of 4.7 mm by 16 mm.

FIG. 25. A lancet was used to puncture the finger of the blood donor and a large pool (approximately 15-40 μL) of blood was allowed to form directly on the finger. A 10 μL glass syringe was used to quantitatively transfer aliquots of blood from the finger to the absorbent material that was held secure by a clamp as depicted in FIG. 25. The clamp contained two wire leads that made contact with both electrodes on the absorbent material. The two wire leads on the clamp were both connected to the Arduino-resistance-measurement device and this device was programmed to output a resistance measurement in 12 second intervals. Data recording was initiated prior to the quantitative blood transfer. The resistance data was exported to a spreadsheet for data processing and analysis.

FIG. 18 Experimental—Conductance Drying Curves

Aliquots of blood at 6, 8, 10, 12 and 14 μL and a hematocrit level of 50 were transferred to separate electrode-containing absorbent material cut outs. Conductance curves were produced for each aliquot and these data were plotted on a single chart, see FIG. 9.

FIG. 19 Experimental—Integrated Conductance vs. Blood Volume

Figure 26:
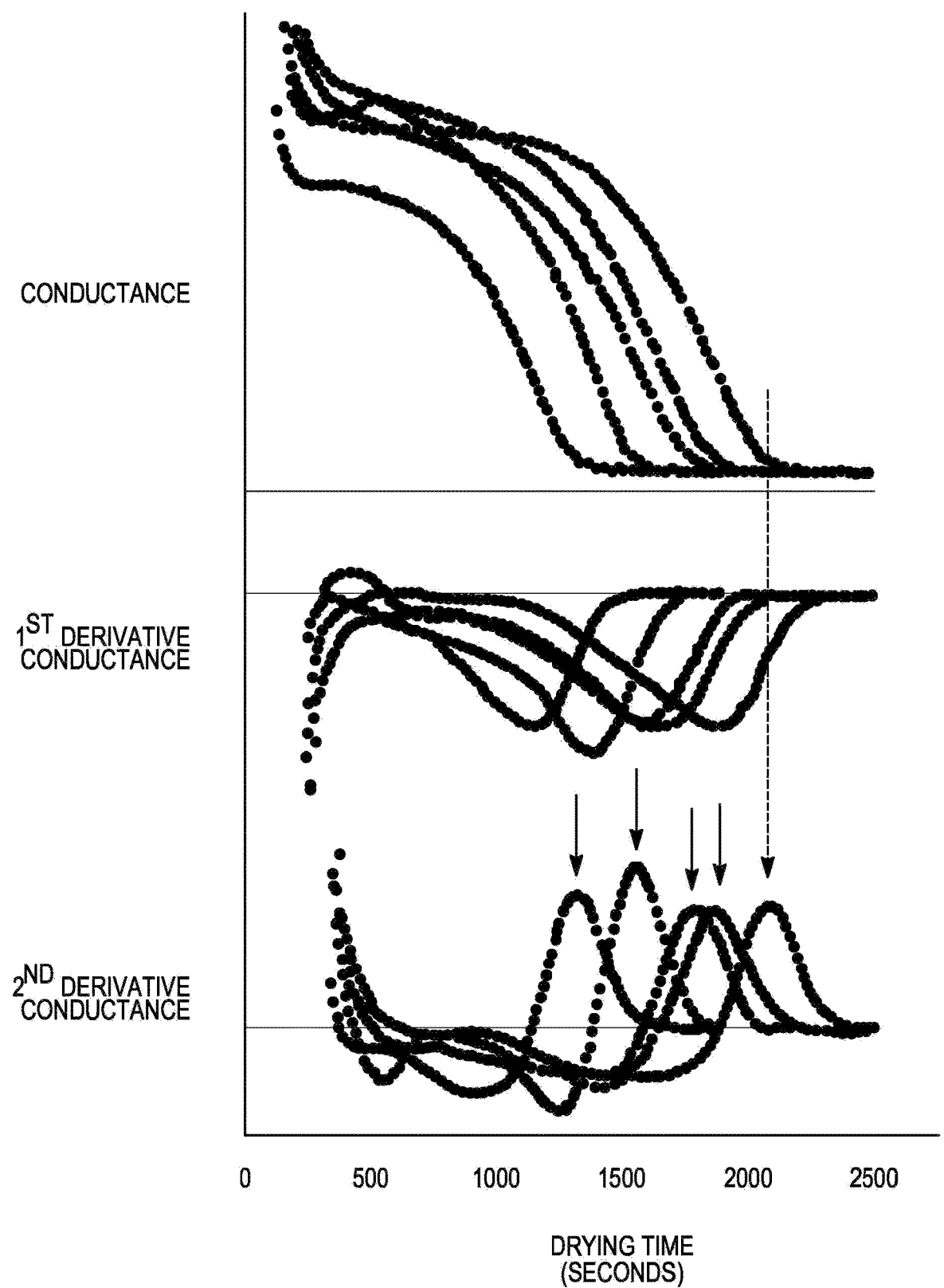

FIG. 26. FIG. 10 was produced by finding the peak top position of the 2nd derivative of the conductance drying curve. FIG. 26 shows the conductance drying curve and a smoothed 1st and 2nd derivative of conductance drying curve. In the 2nd derivative plot, five arrows indicate the peak top position or the "drying-end-point" corresponding to each curve. A long vertical dashed arrows is positioned near the end point of the 14 μL drying curve and this illustrates how the how the conductance drying curve corresponds to its 2nd derivative peak top or the drying-end-point. These five drying-times were used to produce FIG. 10.

Figure 27:
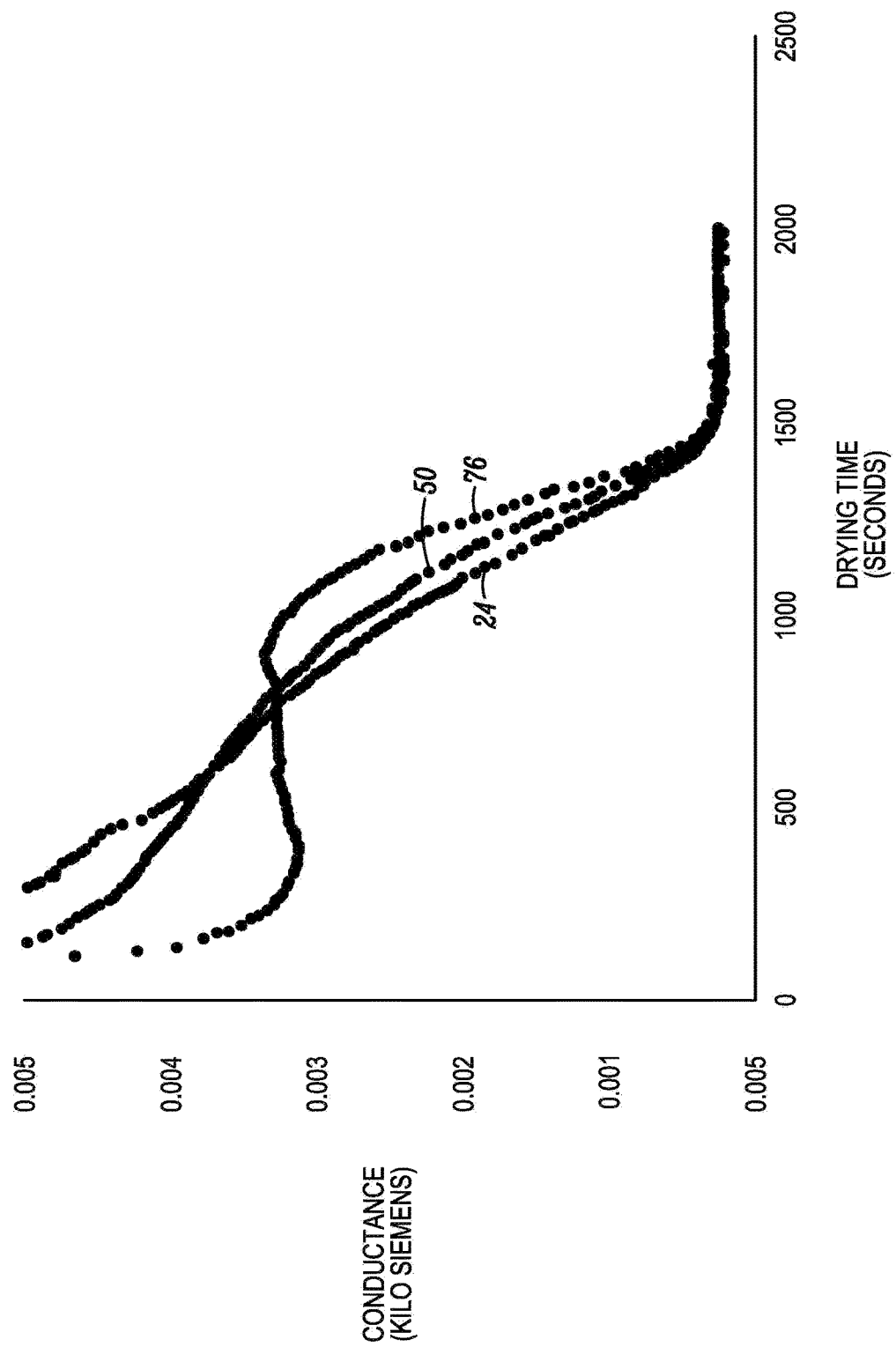
FIG. 27 shows that the drying-time is highly independent of the hematocrit level, according to an example embodiment.

FIG. 27. shows that the drying-time is highly independent of the hematocrit level. The three conductance drying curves shown here, were produced by loading 8 μL of blood onto the absorbent material. The blood used was at hematocrit levels of 24, 50 and 76 as indicated in this figure. The region of the curves to the left of the "drying-end-point" vary significantly, however there is a high level of agreement, between the three curves, as the curve approaches the drying-end-point. There is complete agreement between the three plots at and to the right of the drying-end-point.

Blood Collection Device Image Analysis & Hematocrit Experiments

FIG. 21 Experimental

These images were collected on a custom built photobooth with a similar configuration as outlined in FIG. 11 and integrated into a PAL-RTC (CTC Analytics AG) robotic sample preparation system. Custom software was used to classify each pixel of the raw images into distinct regions.

FIG. 22 Experimental

A 90 blood collection devices were loaded with blood at six volumes: 5, 7.5, 10, 12, 12.5 and 15 µL and at five hematocrit levels: 24, 36, 44, 56, 64 and 76. Therefore thirty combinations of blood volumes and hematocrits levels were produced and for each of these combinations three replicated blood collection devices were loaded and processed accordingly and this resulted in the analysis of 90 blood collection devices. The blood was produced at specific hematocrit levels according to the publication entitled: "What is the right blood hematocrit preparation procedure for standards and quality control samples for dried blood spot analysis?" (Bioanalysis. 2015; 7(3):345-51). The error bars in FIG. 13 represent one standard deviation for the fifteen values that were produced at each hematocrit level.

The mathematical model used was to model the data described in 13.1.3 was in the form of:

$$\text{volume} = p1 + p2*\text{area} + p3*IR + p4*\text{area}*IR + p5*IR^2 + p6*\text{area}*IR^2 + p7*IR^3$$

Here p1, p2, p3, p4, p5, p6 and p7 are all fitting parameters.

Figure 28:
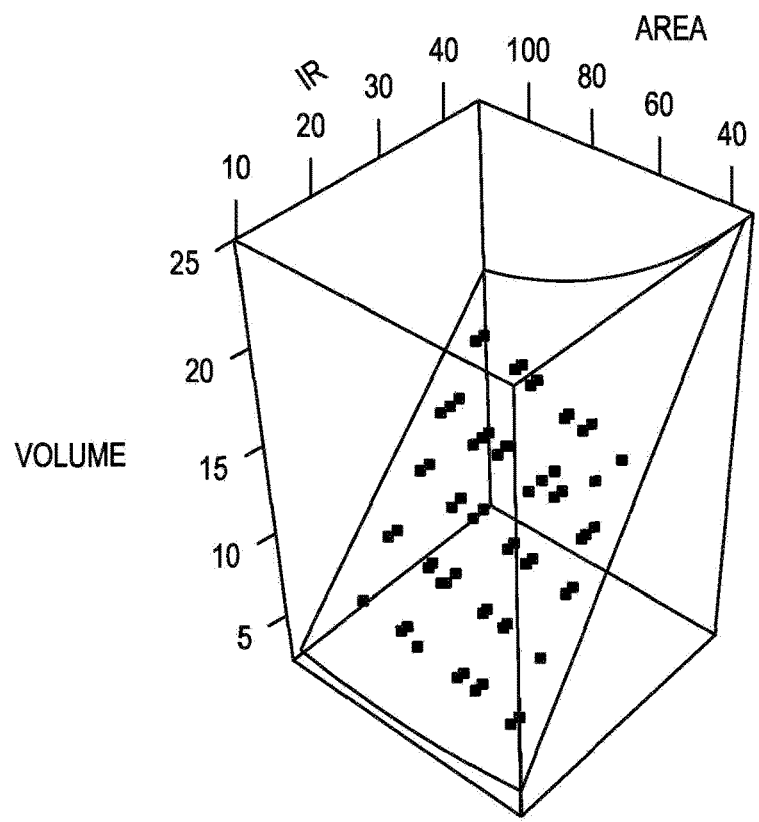
FIG. 28 is a plot of data produced from analysis of the ninety blood loaded blood collection devices, according to an example embodiment.

FIG. 28. is a plot of data produced from analysis of the ninety blood loaded blood collection devices that were described above. This 3-dimensional plot has the axes: 1) blood-region-area in $mm^{2,}$ $^2$) average of all the IR green-channel values for pixels in the blood region and 3) the blood loading volumes in microliters. Each of the 90 points are represented by a black square. The 3-dimensional mathematical model, described above, was used to produce the gray surface displayed in this figure.

Figure 29:
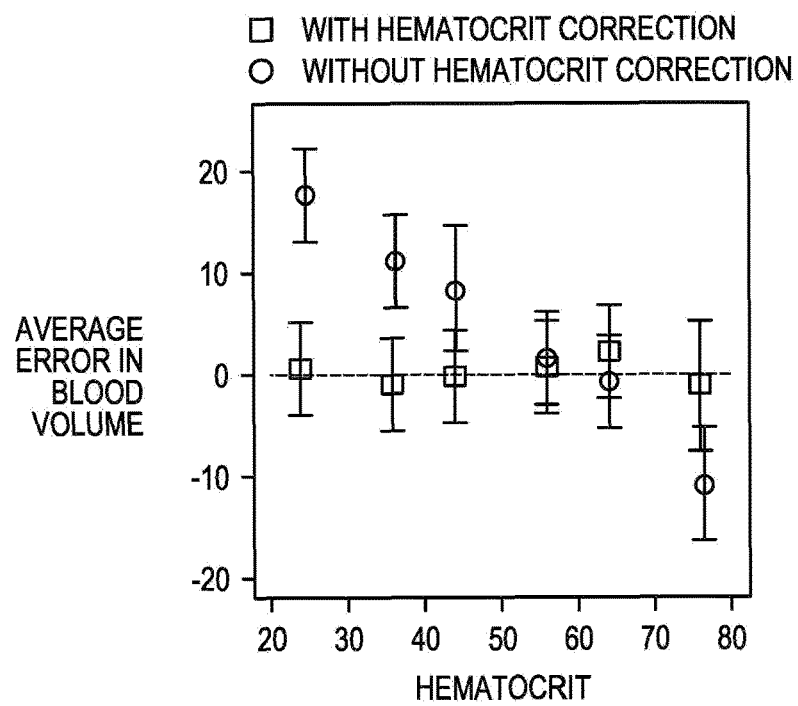
FIG. 29 shows the error related to the volume determination when IR hematocrit correction was used and when IR hematocrit correction was not used, according to an example embodiment.

FIG. 29. shows the error related to the volume determination when IR hematocrit correction was used and when IR hematocrit correction was not used.

While the embodiments have been described in terms of several particular embodiments, there are alterations, permutations, and equivalents, which fall within the scope of these general concepts. It should also be noted that there are many alternative ways of implementing the methods and apparatuses of the present embodiments. It is therefore intended that the following appended claims be interpreted as including all such alterations, permutations, and equivalents as fall within the true spirit and scope of the described embodiments.

What is claimed:

1. A method of collecting blood samples comprising:
   positioning an absorbent material within a housing, the housing having an open end and a capped end, the absorbent sample material positioned near the open end of the housing;
   contacting a source of blood through the opening in the housing without moving the absorbent sample material with respect to the housing, the absorbent material attached to a cap at the capped end;
   holding the blood absorbed by absorbent sample material within the housing to dry;
   measuring the volume of blood absorbed by the absorbent sample material; and
   removing the cap and the attached absorbent material;
   placing the absorbent material in solvents to test the blood while the cap remains attached to the absorbent material, wherein measuring the volume of the blood on the absorbent sample material includes:
      measuring the start time when blood is absorbed on the absorbent sample material; and
      measuring the conductance of the absorbent sample to determine a drying time.

2. The method of claim 1 further comprising shipping the housing and the absorbent material to a lab location.

3. The method of claim 1 wherein holding the sample with the housing includes:
   attaching one end of the absorbent sample material to one end of the stem; and
   attaching another end of the stem to the cap of the housing, the length of the stem selected to position a free end of the absorbent material near an opening in the housing.

4. The method of claim 3 further comprising labeling the stem with an identifier.

5. The method of claim 3 further comprising:
   removing the stem and absorbent sample material from the housing with a robot; and
   moving the stem and absorbent sample material using the robot, the stem and absorbent sample material moved to at least one different position to complete a test of a dried blood portion on the absorbent sample material.

6. The method of claim 1 wherein holding the sample with the housing includes:
   attaching the absorbent material to a stem; and
   attaching a portion of the stem to the cap positioned over a first opening in the housing, the length of the stem selected to position a portion of the absorbent material near a second opening in the housing.

7. The method of claim 1 wherein measuring the volume of the blood on the absorbent sample material includes measuring an electrical property of the absorbent sample material.

8. The method of claim 1 wherein measuring the volume of the blood on the absorbent sample material includes measuring the conductance of the absorbent sample.

9. The method of claim 1 wherein the volume of the blood on the absorbent sample material is related to the drying time of the absorbent sample.

10. The method of claim 1 further comprising illuminating the absorbent sample material with another light source that reacts with components in the dried blood to produce the first color.

11. The method of claim 1 further comprising taking a digital image of the absorbent sample material and counting the number of pixels of the first color.

* * * * *